(12) United States Patent
Shibley et al.

(10) Patent No.: US 12,089,866 B2
(45) Date of Patent: Sep. 17, 2024

(54) CURETTE AND USE THEREOF

(71) Applicant: Atropolos Limited, Bray (IE)

(72) Inventors: Kirk Anthony Shibley, Wayzata, MN (US); Lucy Dolores Halpin, Rathfarnham (IE); Frank Bonadio, Bray (IE); Olwen Coughlan, Kihnacanogue (IE)

(73) Assignee: Atropos Limited, Bray (IE)

( * ) Notice: Subject to any disclaimer, the term of this patent is extended or adjusted under 35 U.S.C. 154(b) by 138 days.

(21) Appl. No.: 17/609,056

(22) PCT Filed: Mar. 16, 2020

(86) PCT No.: PCT/EP2020/057053
§ 371 (c)(1),
(2) Date: Nov. 5, 2021

(87) PCT Pub. No.: WO2020/187823
PCT Pub. Date: Sep. 24, 2020

(65) Prior Publication Data
US 2022/0233211 A1    Jul. 28, 2022

Related U.S. Application Data

(60) Provisional application No. 62/935,924, filed on Nov. 15, 2019, provisional application No. 62/820,606, filed on Mar. 19, 2019.

(51) Int. Cl.
*A61B 17/3207*    (2006.01)

(52) U.S. Cl.
CPC ............ *A61B 17/320708* (2013.01)

(58) Field of Classification Search
CPC .......... A61B 17/320708; A61B 17/442; A61B 17/4241; A61B 17/42; A61B 17/3207; A61B 2017/4216; A61B 2017/320716; A61B 2017/4225; A61B 2090/3925; A61B 2217/005; A61B 90/00
See application file for complete search history.

(56) References Cited

U.S. PATENT DOCUMENTS 3,670,732 A * 6/1972 Robinson ....... A61B 17/320708
604/105
3,848,602 A * 11/1974 Gutnick ................. A61B 17/42
604/104
5,759,154 A   6/1998 Hoyns
(Continued)

FOREIGN PATENT DOCUMENTS

JP       S5038979 A     4/1975
JP       S55125859 A    9/1980
(Continued)

OTHER PUBLICATIONS

International Search Report and Written Opinion in corresponding Application No. PCT/EP2020/057053, dated Jun. 17, 2020, (12 pages).

*Primary Examiner* — Jocelin C Tanner
(74) *Attorney, Agent, or Firm* — Bookoff McAndrews, PLLC

(57) ABSTRACT

An echogenic curette for carrying out a suction dilation and curettage allows the physician to view the curette and the pathology they want to remove, and use that to guide the procedure. The echogenic curette is visible using ultrasound imaging.

17 Claims, 36 Drawing Sheets

(56) References Cited

U.S. PATENT DOCUMENTS

| | | | |
|---|---|---|---|
| 6,210,330 B1* | 4/2001 | Tepper | A61B 17/4241 600/463 |
| 8,679,133 B2* | 3/2014 | Peterson | A61B 17/320708 606/131 |
| 2009/0048537 A1 | 2/2009 | Lydon et al. | |
| 2011/0190595 A1* | 8/2011 | Bennett | A61B 1/05 600/300 |
| 2012/0022314 A1 | 1/2012 | Sing et al. | |
| 2012/0095404 A1* | 4/2012 | Massengale | A61B 8/481 604/528 |
| 2014/0121658 A1* | 5/2014 | Cosman, Jr. | A61B 18/18 606/33 |
| 2014/0221828 A1 | 8/2014 | McKinnis et al. | |
| 2014/0364698 A1* | 12/2014 | Nadershahi | A61B 1/008 600/215 |
| 2015/0374348 A1* | 12/2015 | Hingston | A61B 8/0841 600/458 |
| 2016/0270819 A1* | 9/2016 | Ahluwalia | A61B 17/4241 |
| 2020/0008840 A1* | 1/2020 | Addis | A61M 25/007 |

FOREIGN PATENT DOCUMENTS

| | | | |
|---|---|---|---|
| JP | 2000507841 A | 6/2000 | |
| JP | 2013116288 A | 6/2013 | |
| JP | 2017514595 A | 6/2017 | |
| WO | WO 2007/089724 A1 | 8/2007 | |
| WO | WO 2015/166081 A1 | 11/2015 | |

* cited by examiner

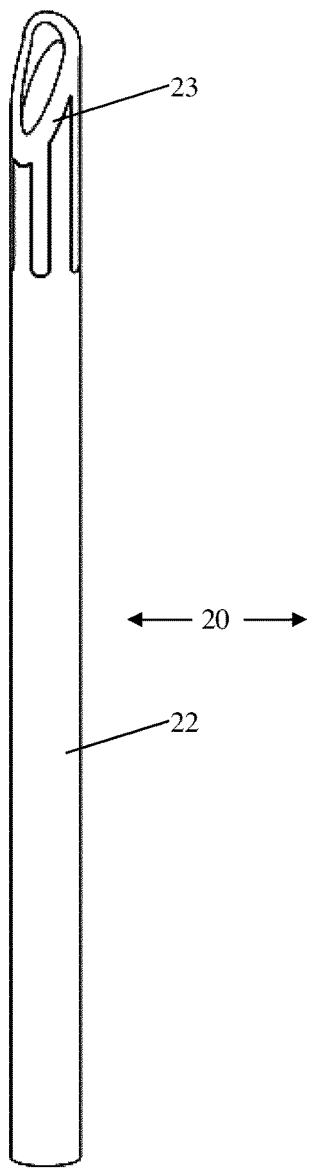  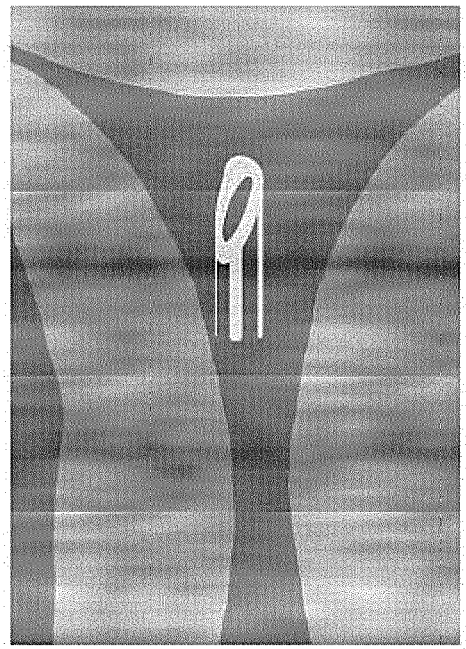
Fig. 11          Fig. 12                    Fig. 13

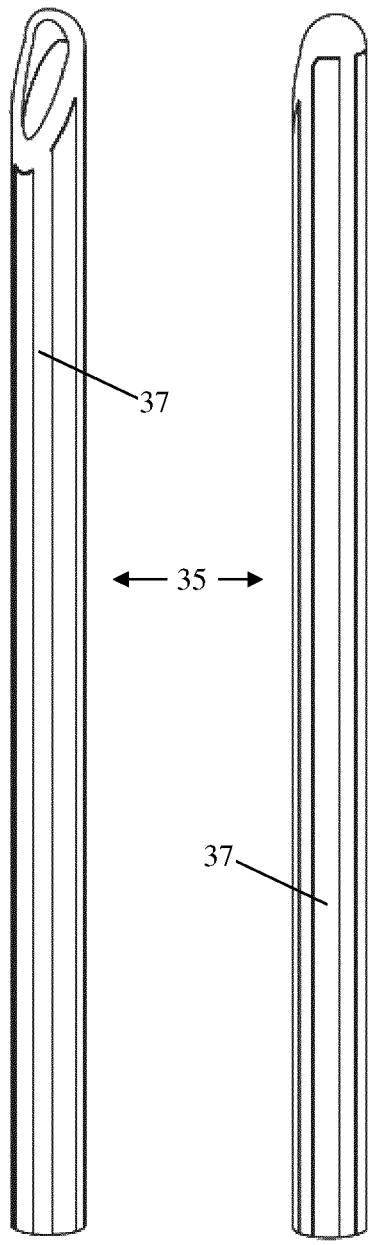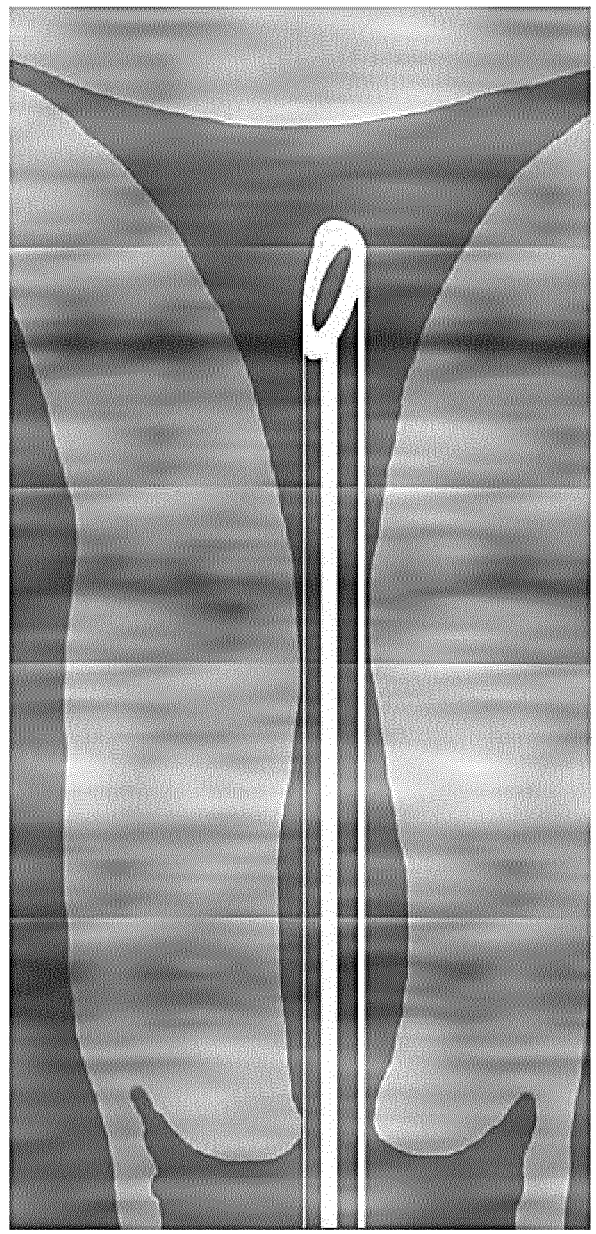
Fig. 18　　Fig. 19　　Fig. 20

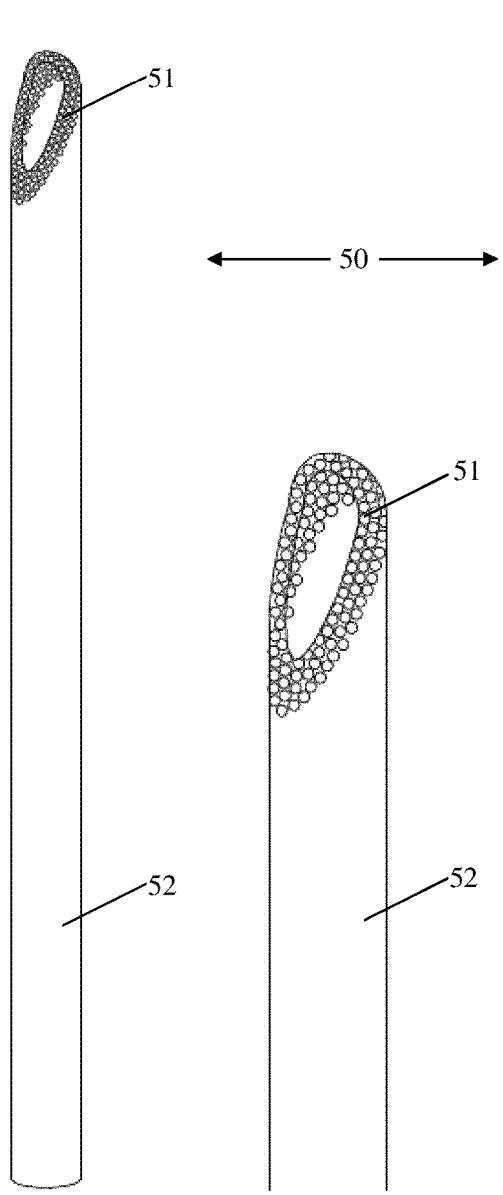 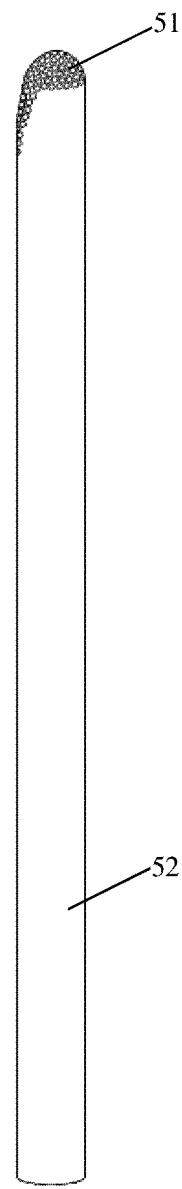 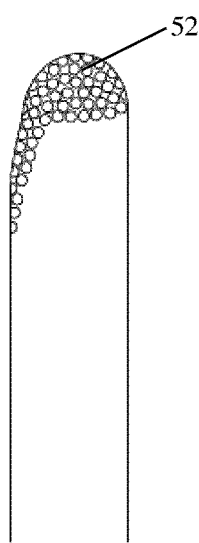
Fig. 24        Fig. 25        Fig. 26        Fig. 27

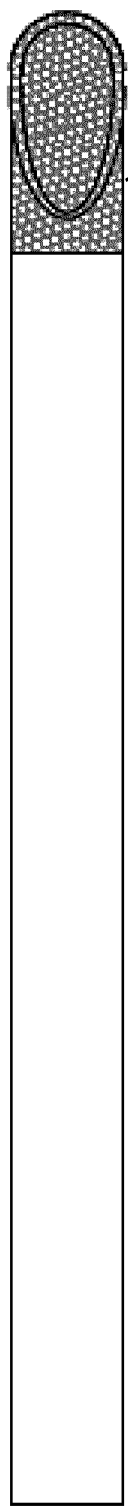
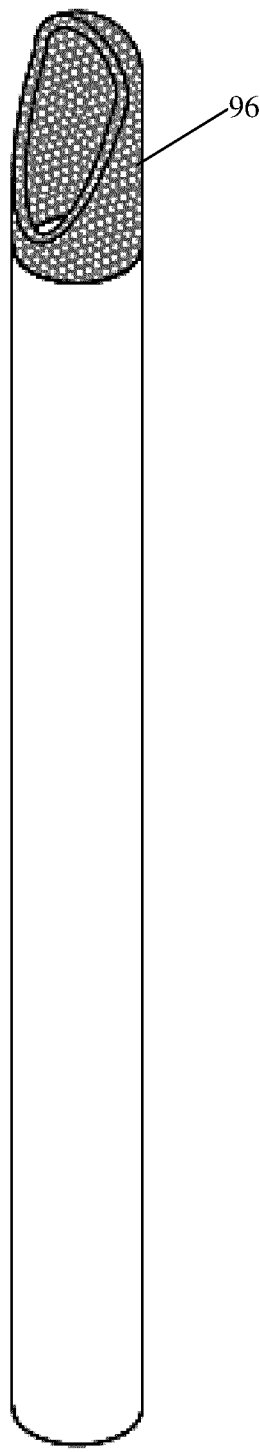
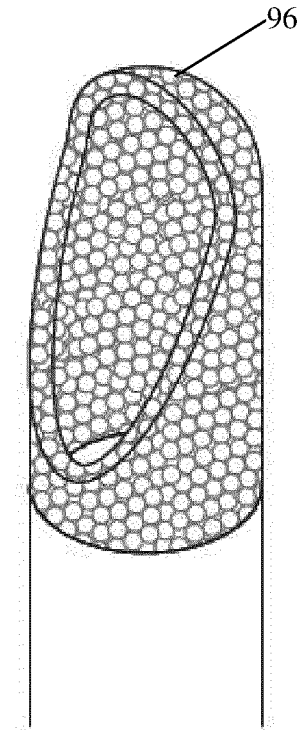
Fig. 61
Fig. 62
Fig. 63

Fig. 67                              Fig. 68

SECTION

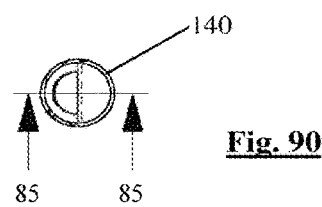
Fig. 90
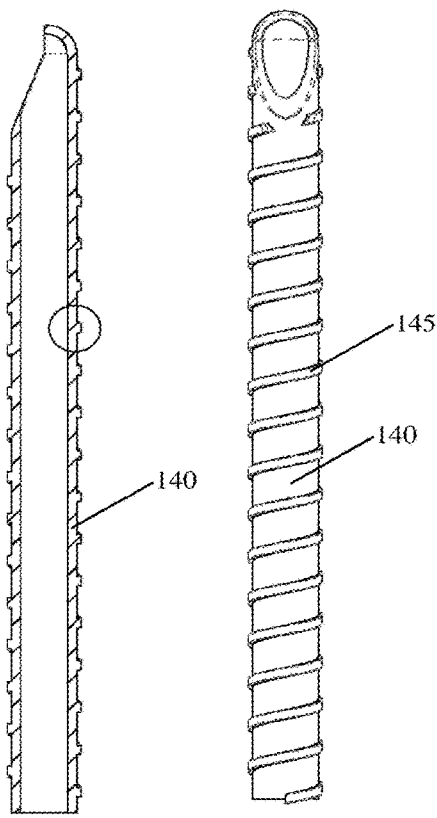
SECTION
Fig. 85
Fig. 86
Fig. 87
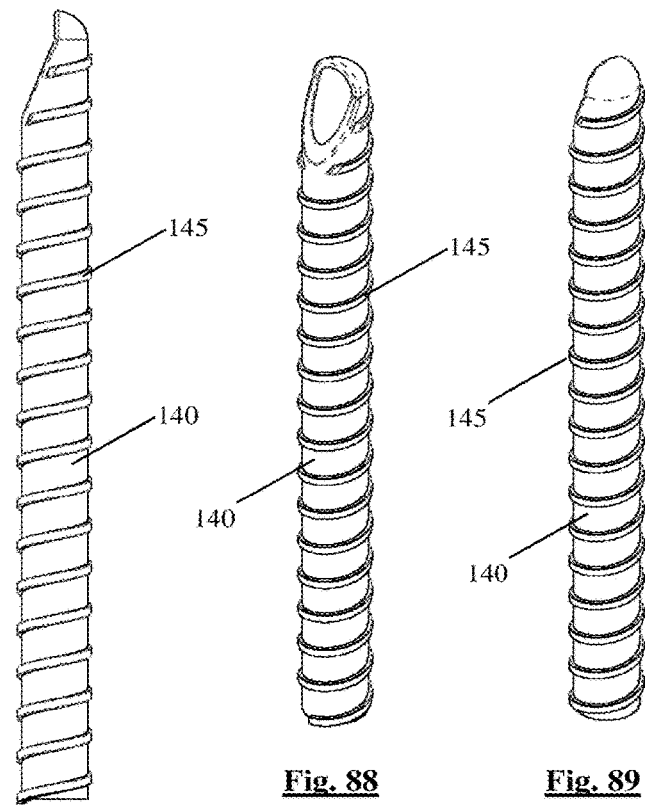
Fig. 88
Fig. 89
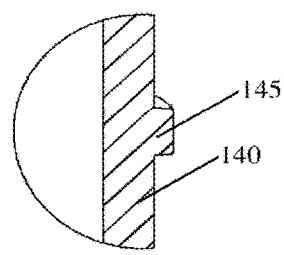
Fig. 91

SECTION

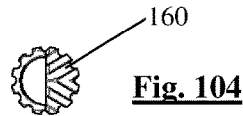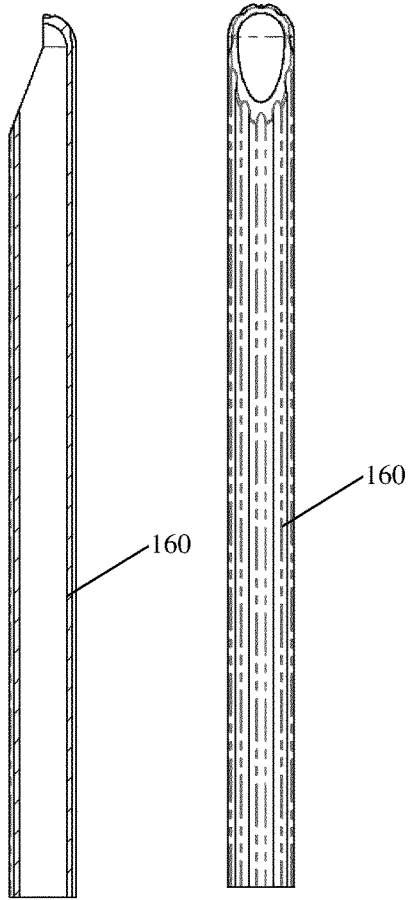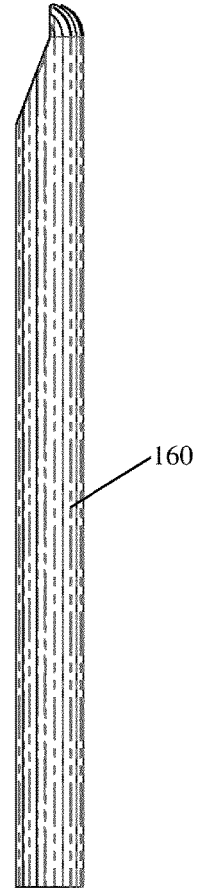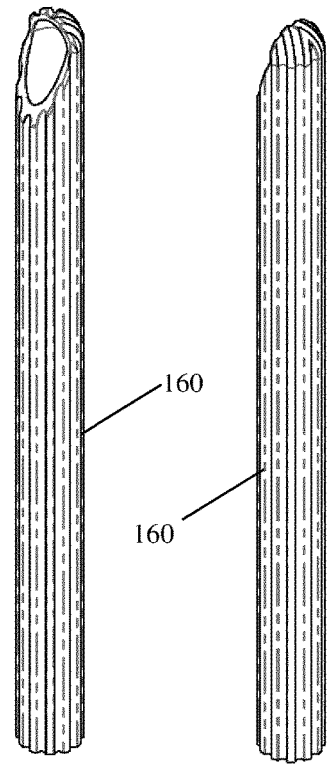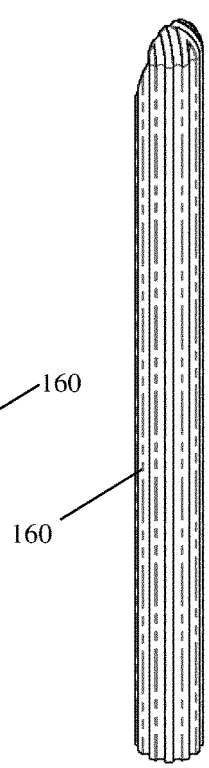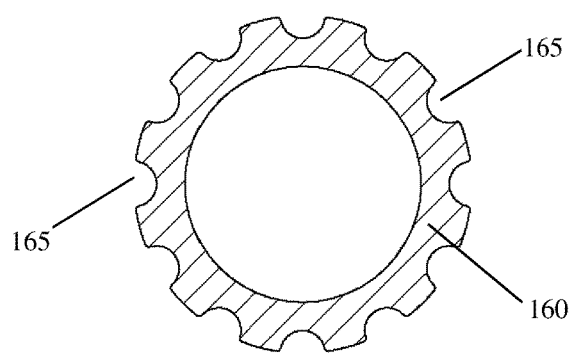

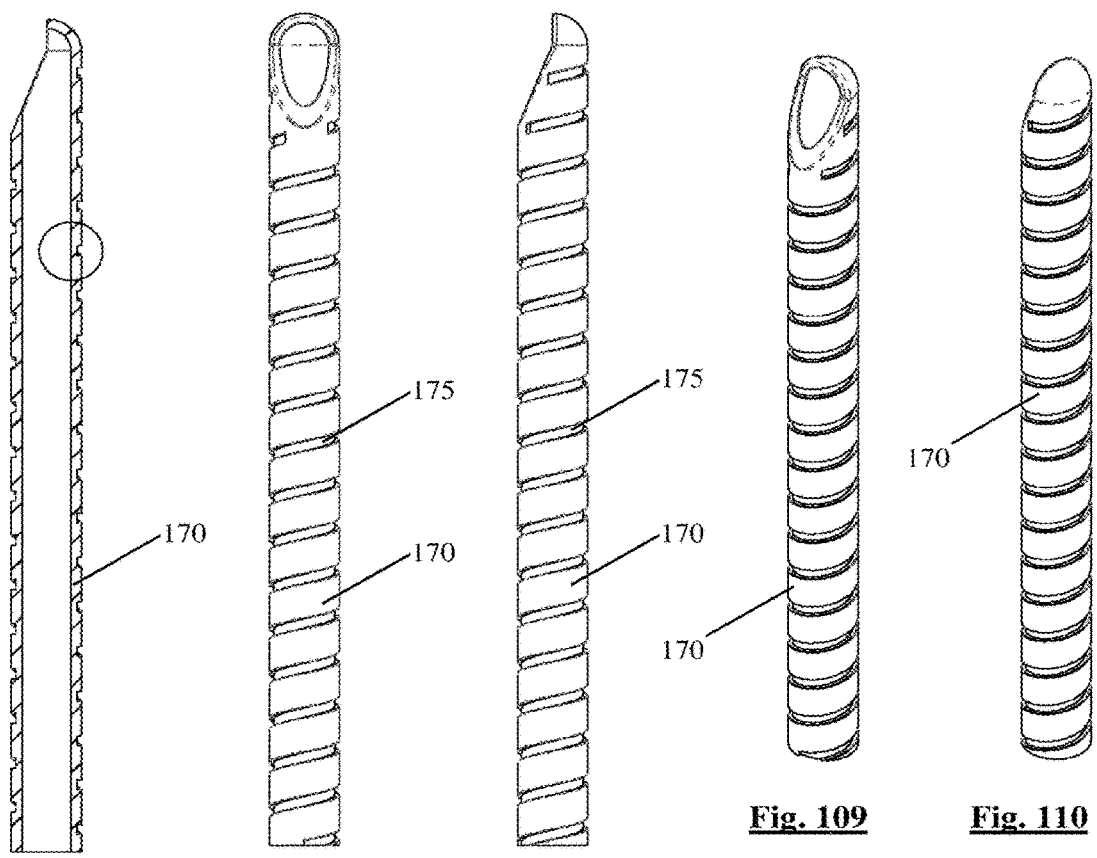

SECTION

SECTION

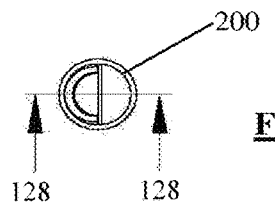
Fig. 133
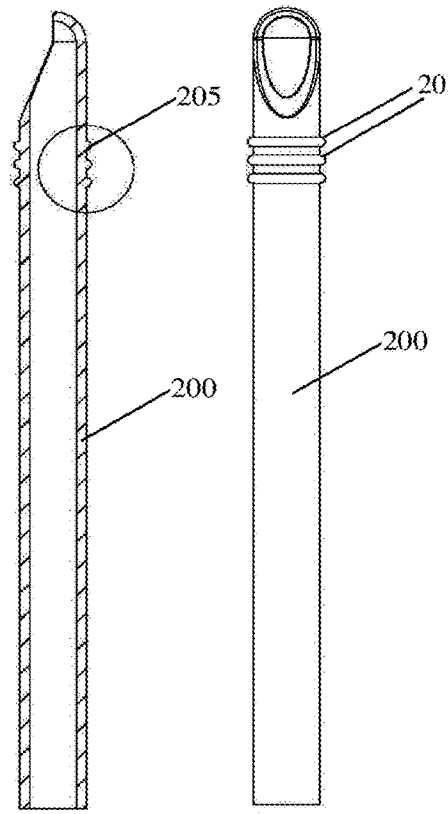
SECTION
Fig. 128
Fig. 129
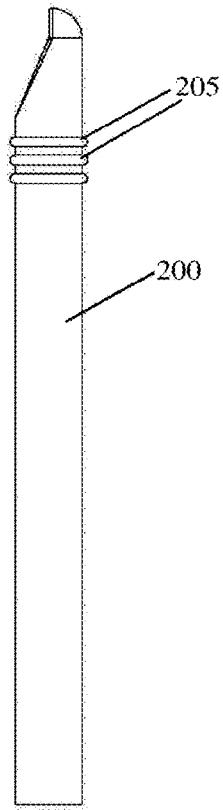
Fig. 130
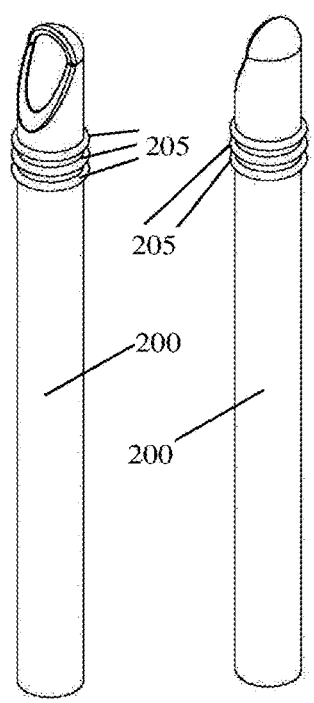
Fig. 131
Fig. 132
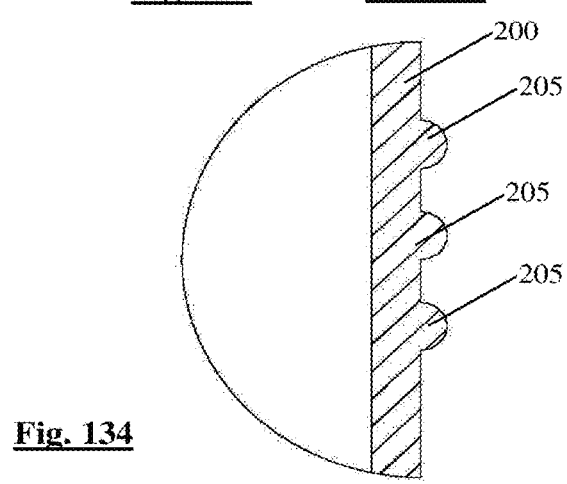
Fig. 134

CURETTE AND USE THEREOF

INTRODUCTION

Physicians do not have a visual reference of a curette when they perform a suction dilation and curettage. The only reference that confirms success of the procedure is when the physician visually sees endometrial material evacuating.

The curette can cause minor and even major damage to the uterine wall.

STATEMENTS OF INVENTION

The invention provides an echogenic curette for carrying out a suction dilation and curettage which allows the physician view the curette and the pathology they want to remove, and use that to guide them. The echogenic curette is visible on an ultrasonic device used outside the body.

The invention provides a method for carrying out a suction dilation and curettage comprising the steps of:
 deploying an echogenic suction curette into the vagina;
 inserting the echogenic curette into the cervix under ultrasound guidance;
 performing uterine evacuation under ultrasound guidance; and
 withdrawing the echogenic curette.

The method may comprise the step of deploying ultrasound abdominally or vaginally.

Complete emptying of the uterus may be confirmed using ultrasound imaging.

In some cases the method comprises the steps of:
 inserting a retractor into the vagina; and
 stabilising the cervix with a cervical stabiliser prior to deploying the echogenic suction curette into the vagina;
 removing the cervical stabilizer; and
 removing the vaginal retractor after withdrawal of the echogenic curette.

The method may comprise the step, prior to insertion of the retractor, of examining the cervix and the uterus bimanually.

The method may comprise dilating the cervix to a desired diameter.

The invention also provides a suction curette comprising a shaft having a distal inlet end with an opening through which material is drawn into the shaft and a proximal discharge outlet end, wherein at least a portion of the curette is echogenic.

In one case at least the distal inlet end is echogenic.

In some cases the curette comprises a lip extending around the distal inlet and the lip is echogenic.

In some cases at least a portion of the shaft is echogenic.

The curette may comprise echogenic features.

In some cases the echogenic features comprise sharp corners which may be cut into the curette, for example, by etching.

The echogenic features may comprise voids in the curette. In some cases at least some of the voids are at least partially filled with an echogenic material such as a gas.

In some cases the features comprise ribs or rods extending along the curette.

The curette may comprise a main body portion and a distal end portion which is bonded to, or integrally formed with, the main body portion. The distal end portion in some cases is overmoulded to the main body portion. The distal end portion may comprise or consist of an echogenic material.

The curette in some cases may be rendered echogenic by a polystyrene material.

The invention also provides a device for use in a medical procedure wherein at least a portion of the device is rendered echogenic by a polystyrene material.

Other aspects and preferred embodiments of the invention are defined and described in the other claims set out below.

BRIEF DESCRIPTION OF THE DRAWINGS

The invention will be more clearly understood from the following description thereof given by way of example only with reference to the accompanying drawings, in which:

FIGS. 11 to 13 are views of a curette with an echogenic distal tip;

FIGS. 18 to 20 are images of a curette with an echogenic distal tip and echogenic features along the shaft of the curette;

FIGS. 24 to 35 are views of a curette with alternative echogenic distal tips;

FIGS. 61 to 63 are views of another curette with a rigid foam distal tip;

FIGS. 67 and 68 are views of a curette with a spark pattern along the curette;

FIGS. 85 to 91 are views of a curette with a flat square rib;

FIGS. 99 to 105 are views of a curette with cut lines;

FIGS. 106 to 112 are views of a curette with a flat square spiral groove;

FIGS. 128 to 134 are views of a curette with rounded ring ribs; and

DETAILED DESCRIPTION

A method for carrying out a suction dilation and curettage comprises inserting a retractor into the vagina and stabilising the cervix with a cervical stabiliser. An echogenic suction curette is then deployed and inserted under ultrasound guidance. A uterine evacuation is performed under ultrasound guidance. The echogenic curette is then withdrawn, the cervical stabiliser and the retractor are removed. Ultrasound is deployed extra abdominally or vaginally during the procedure and emptying of the uterus is confirmed using ultrasound imaging.

Figure 1:
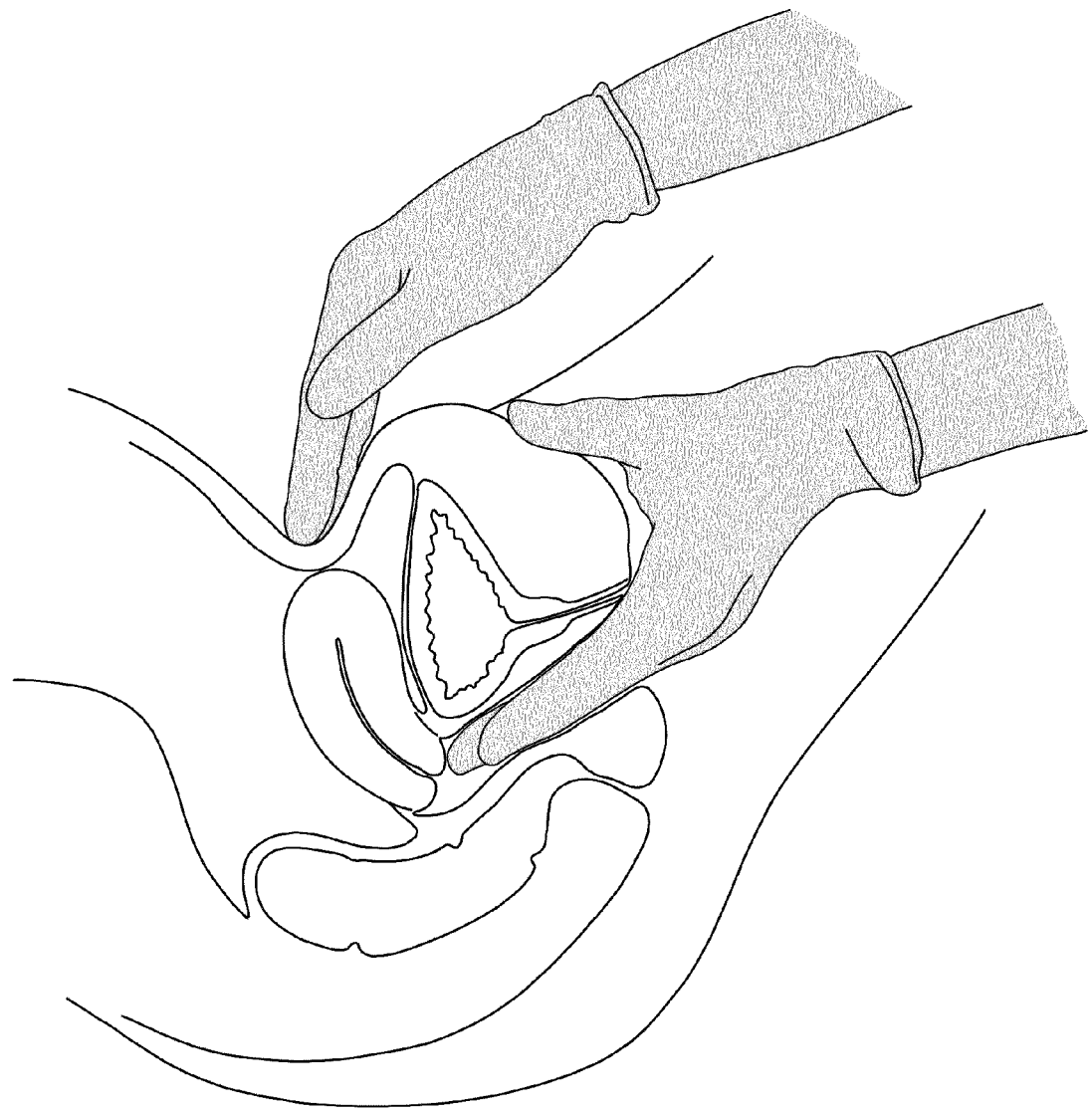
FIG. 1 is a diagram illustrating the step of bi-manual examination of the cervix and uterus.

FIG. 1 illustrates the step of bi-manual examination of the cervix and uterus.

Figure 2:
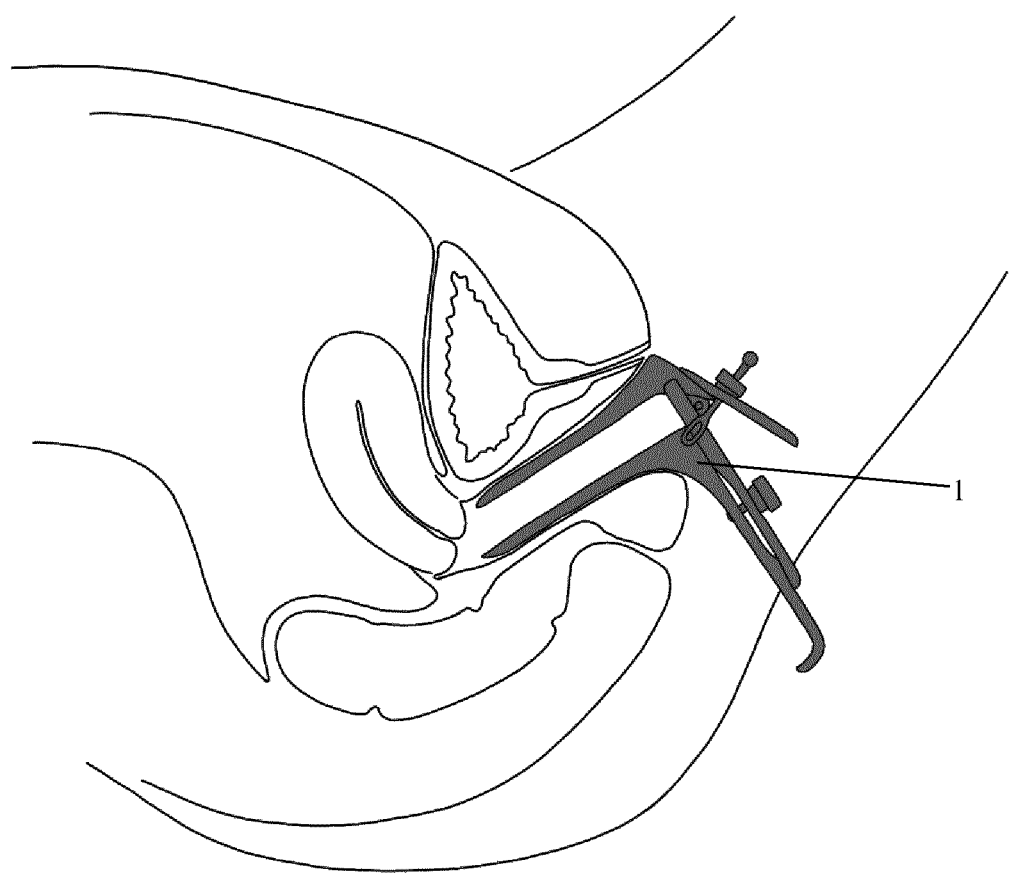
FIG. 2 is a diagram illustrating the placement of a vaginal retractor, for example using a speculum.

FIG. 2 illustrates the placement of a vaginal retractor 1, for example, using a speculum.

Figure 3:
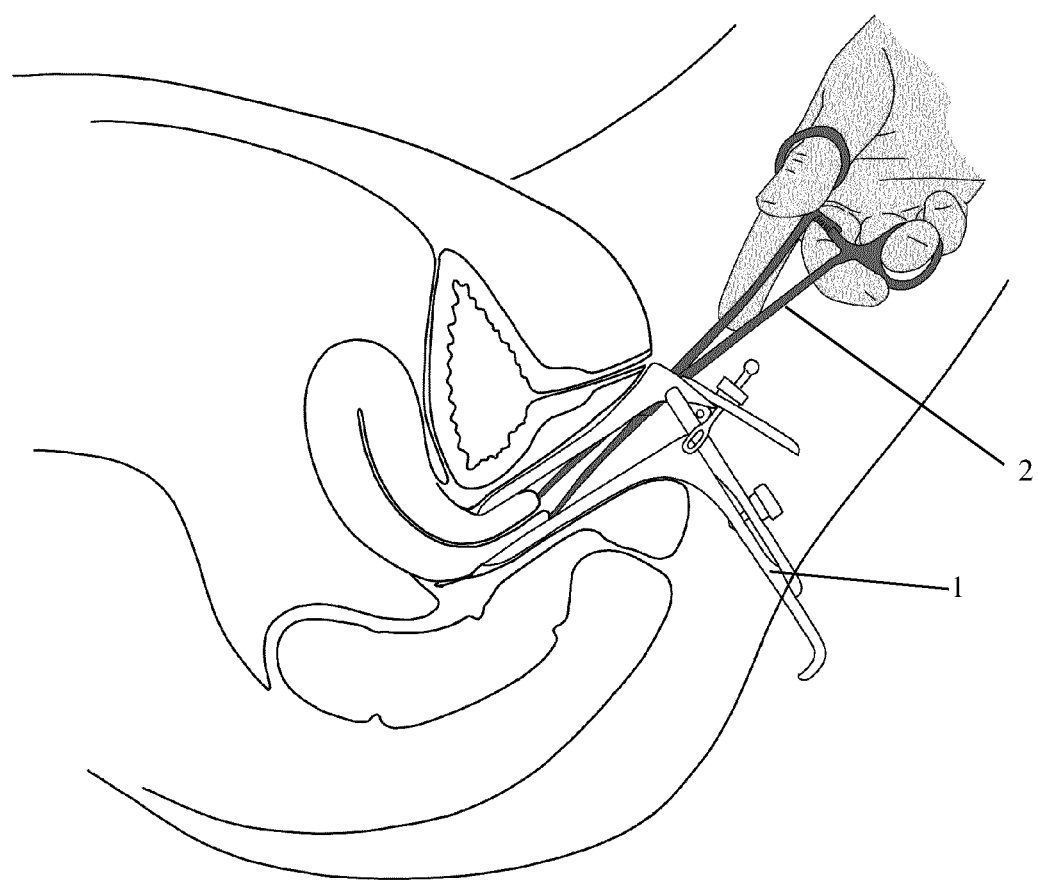
FIG. 3 is a diagram illustrating stabilisation of the cervix, for example, using tenaculum.

FIG. 3 illustrates stabilisation of the cervix, for example, using a tenaculum 2.

Figure 4:
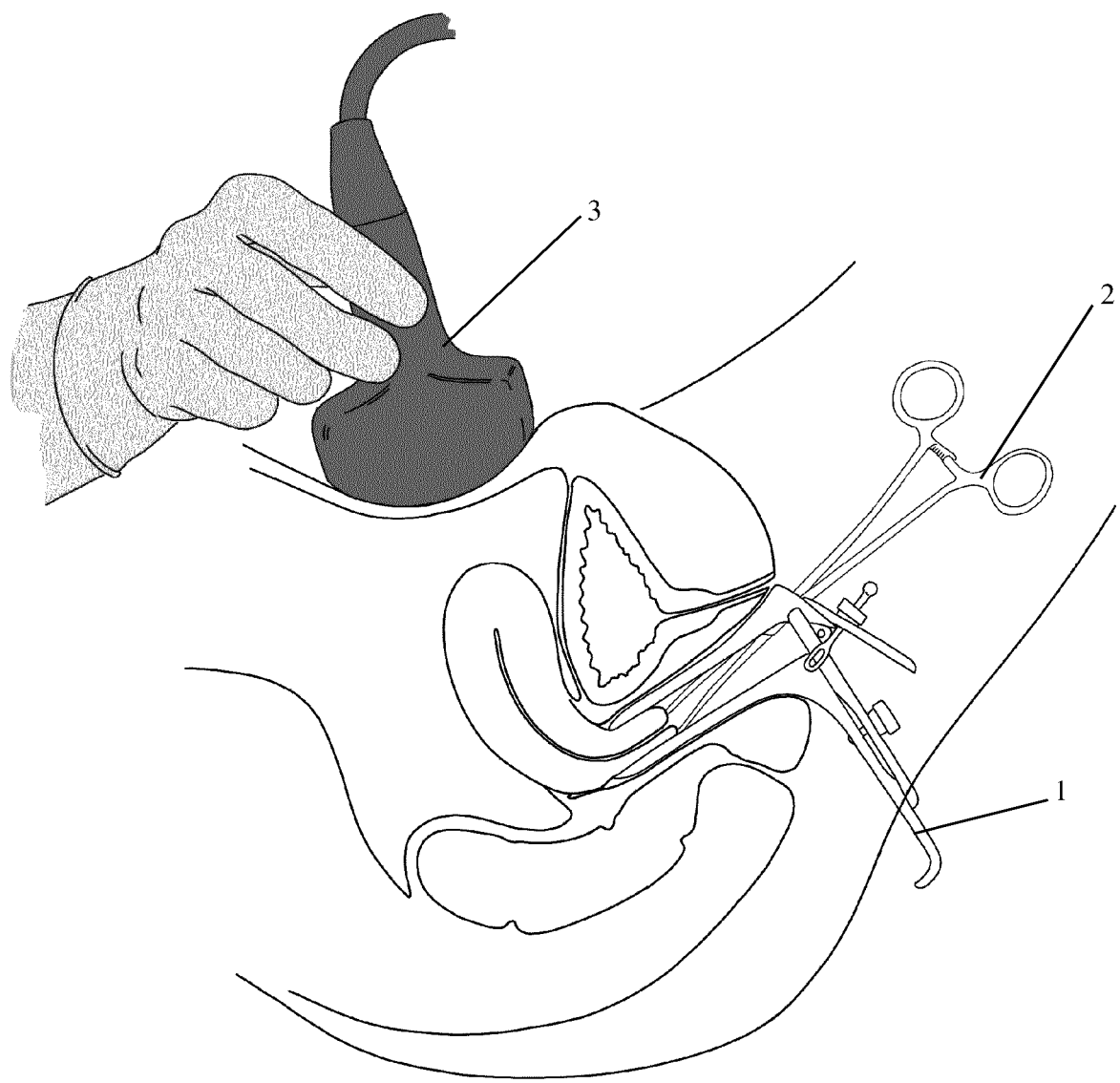
FIG. 4 is a diagram illustrating deployment of ultrasound abdominally.

FIG. 4 illustrates deployment of ultrasound 3 abdominally. Ultrasound may also be deployed vaginally.

Figure 5:
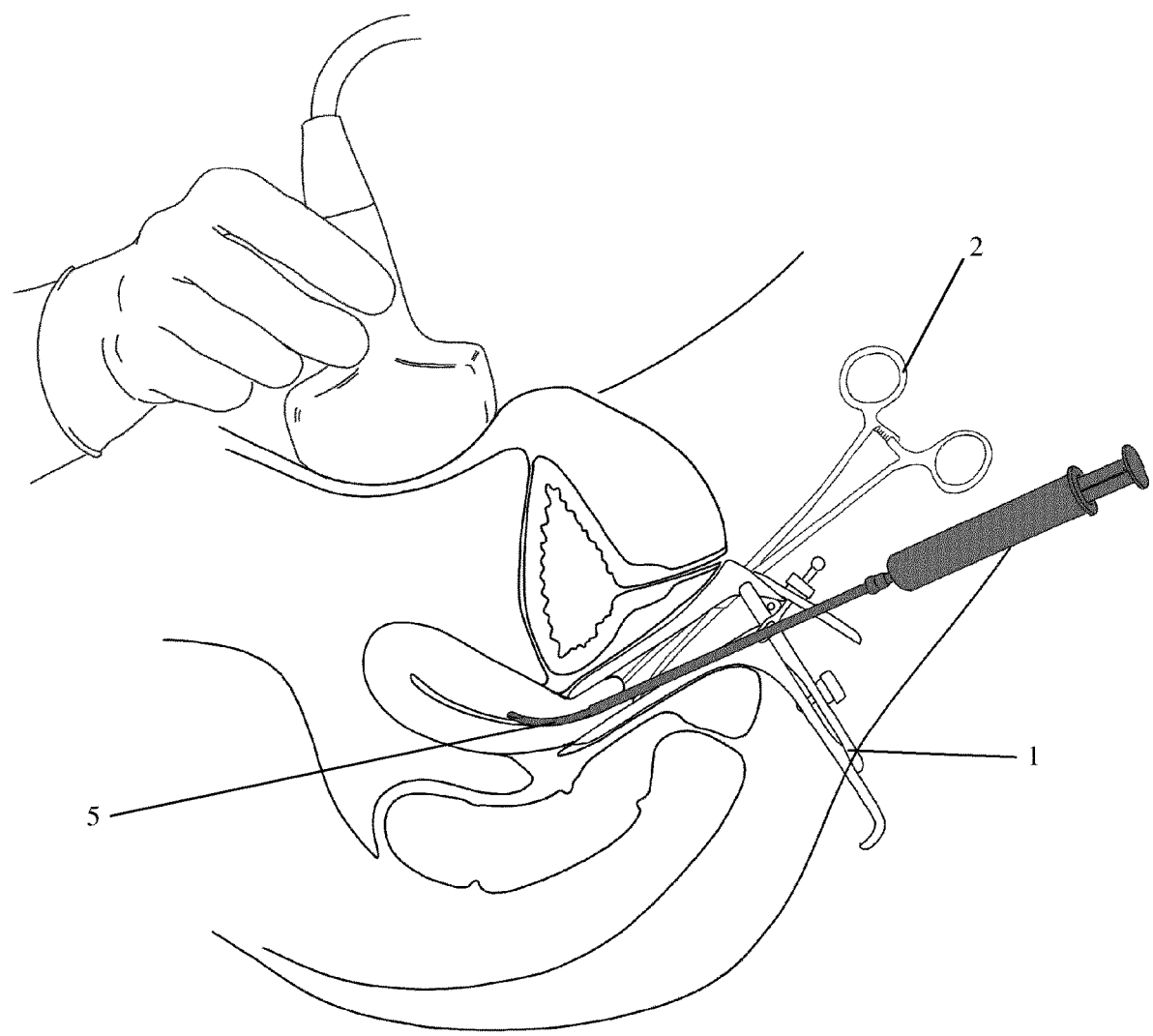
FIG. 5 is a diagram illustrating insertion of an echogenic curette into the cervix under ultrasound guidance.
Figure 6:
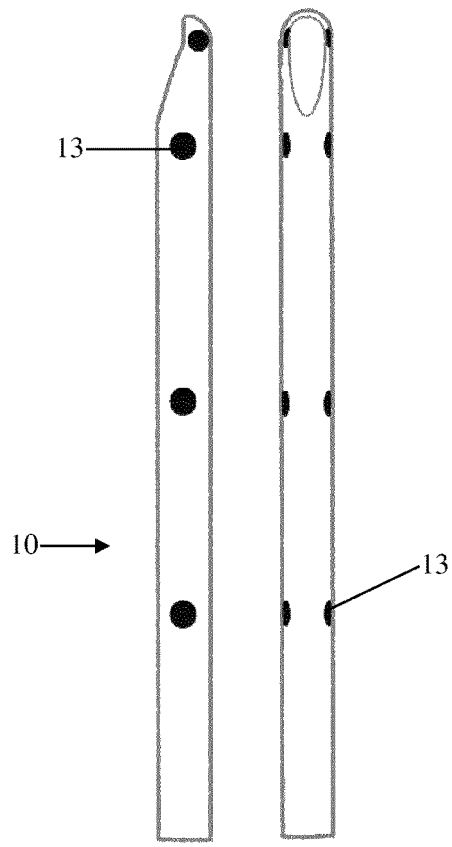
FIGS. 6 to 10 illustrate a curette having echogenic features.
Figure 7:
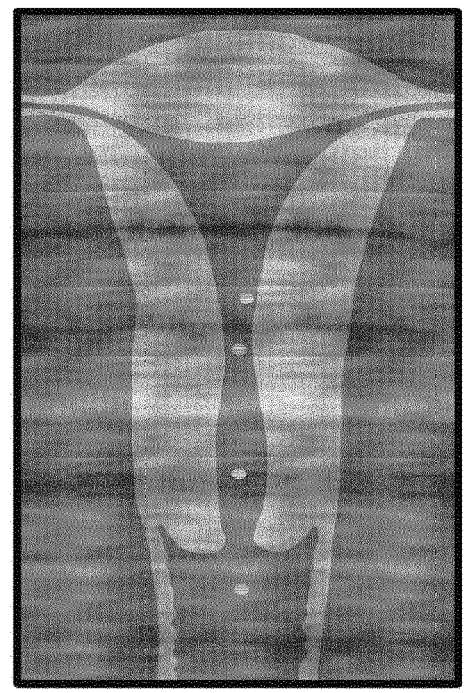
Figure 8:
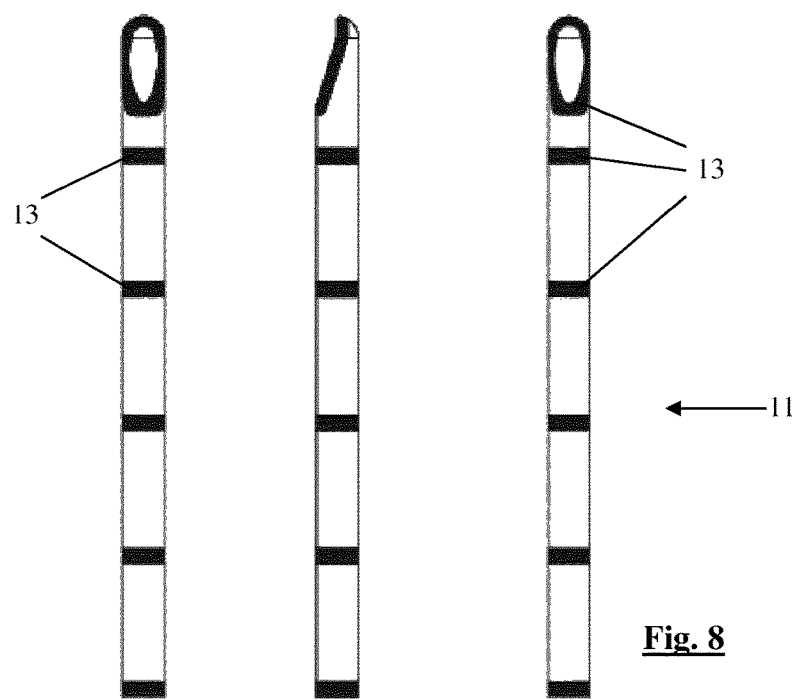
Figure 9:
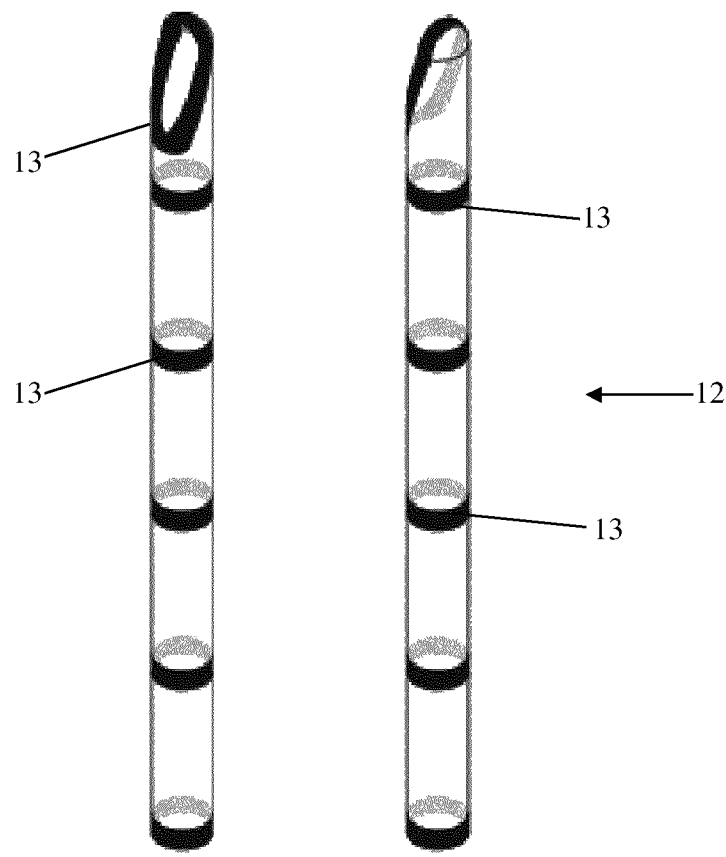
Figure 10:
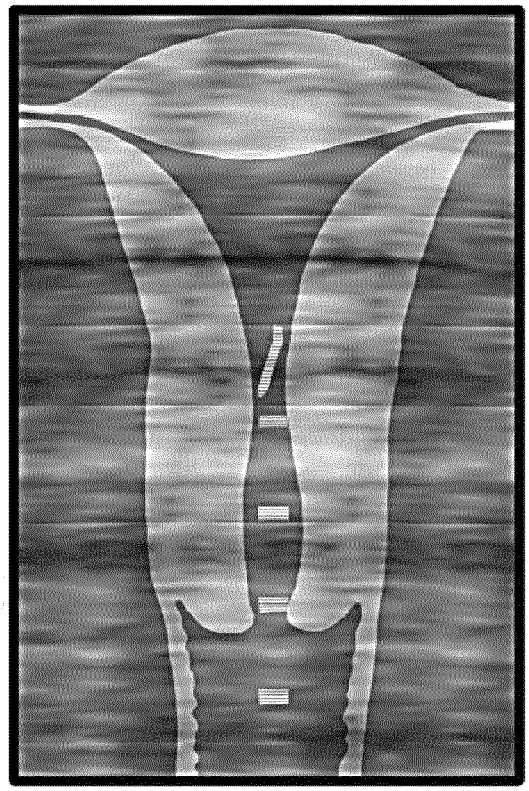
Figure 14:
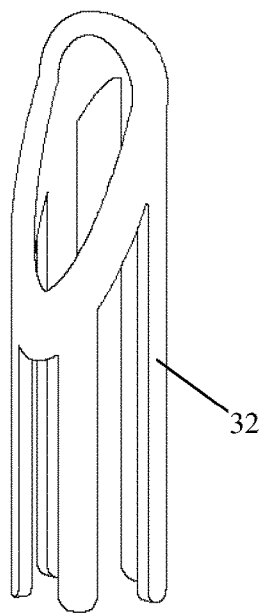
FIGS. 14 to 17 are views of another curette with an echogenic distal tip.
Figure 15:
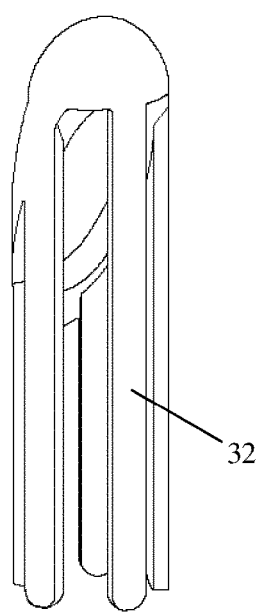
Figure 16:
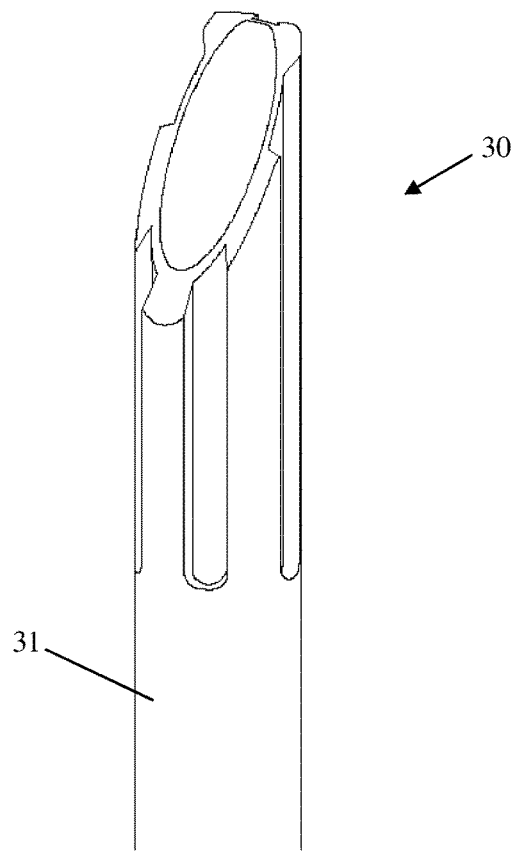
Figure 17:
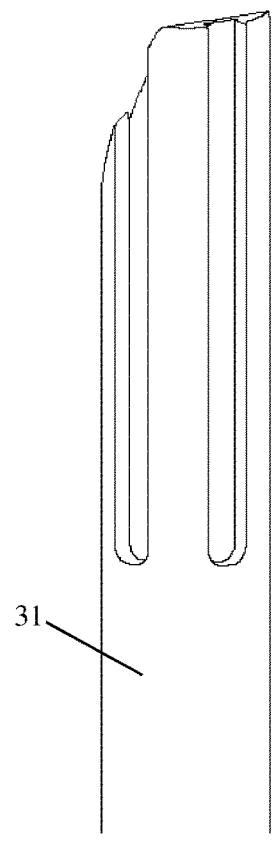

FIG. 5 illustrates insertion of an echogenic curette 5 into the cervix under ultrasound guidance.

To enhance echogenicity of the curette a number of features may be employed either individually or in any suitable combination.

The curette may have empty cavities and/or bubbles which are echo-dense or echo-enhanced under ultrasound. Fluid filled cavities appear black under ultrasound as they offer no resistance to sound-waves. Under ultrasound we have found that polystyrene appears as an echo-enhanced scatter without causing heavy shadowing. An overmoulded component may be mixed into the rigid clear material typically in the form of flakes or balls. The shaft may be a rigid clear material such as polycarbonate or the like. Closed cell foam may be used as it appears as echo-dense or echo-enhanced under ultrasound, similar to the empty cavities. Surface finishes such as moulded in features with sharp edges may be used to cause scatter in the ultrasound which appear echo-dense or echo-enhanced.

The curette, in some cases, may comprise a polymeric material such as polycarbonate, polyethylene or polypropylene. Polystyrene may be incorporated to render the curette echogenic.

In some cases polystyrene, for example in the form of beads is embedded in polycarbonate, polyethylene or polypropylene.

Cavities or bubbles may be formed in or incorporated into the curette using techniques such as described in U.S. Pat. No. 5,160,674, the entire contents of which are incorporated herein by reference.

Referring to FIGS. 6 to 10 there are illustrated various echogenic curettes 10, 11, 12. The black areas 13 on the curettes represent either an echogenic coating or features that allows the ultrasound equipment to see the parts. The markings 13 assist surgeons in seeing the depth and orientation of the curette for the removal of tissue.

Referring to FIGS. 11 to 13, in this case a curette 20 has a distal tip 21 and the tip profile has a material with more echogenicity than that of the shaft 22 which is overmoulded onto the tip. The tip 21 may, for example, comprise polystyrene or closed cell foam which will contrast to the material of the shaft 22. The shaft may be of polycarbonate.

FIGS. 14 to 17 illustrate a curette 30 comprising a shaft 31 and an overmoulded component 32.

FIGS. 18 to 20 are illustrations of another curette 35 with an overmoulded component which, in this case, comprises elongate ribs 37 that extend along the shaft.

Figures 21, 22:
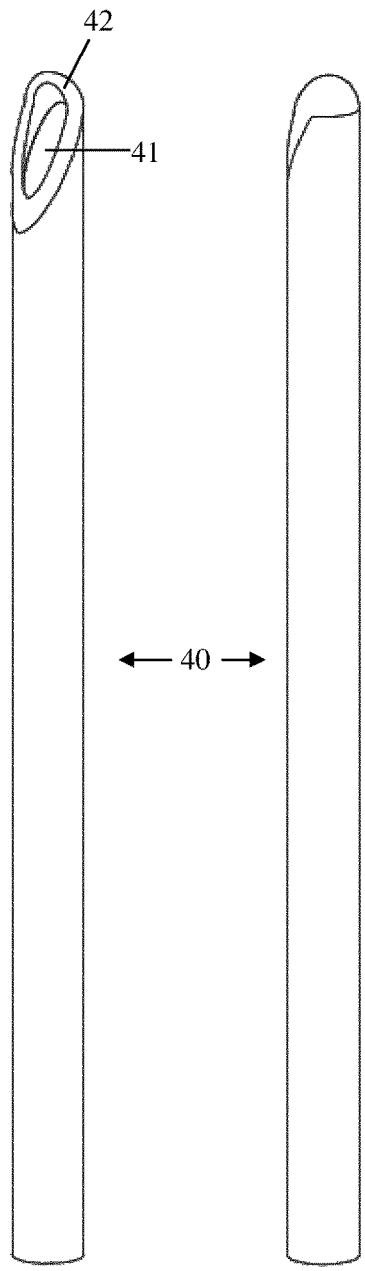
FIGS. 21 to 23 are views of a curette with echogenic features at the distal tip defining the inlet opening.
Figure 23:
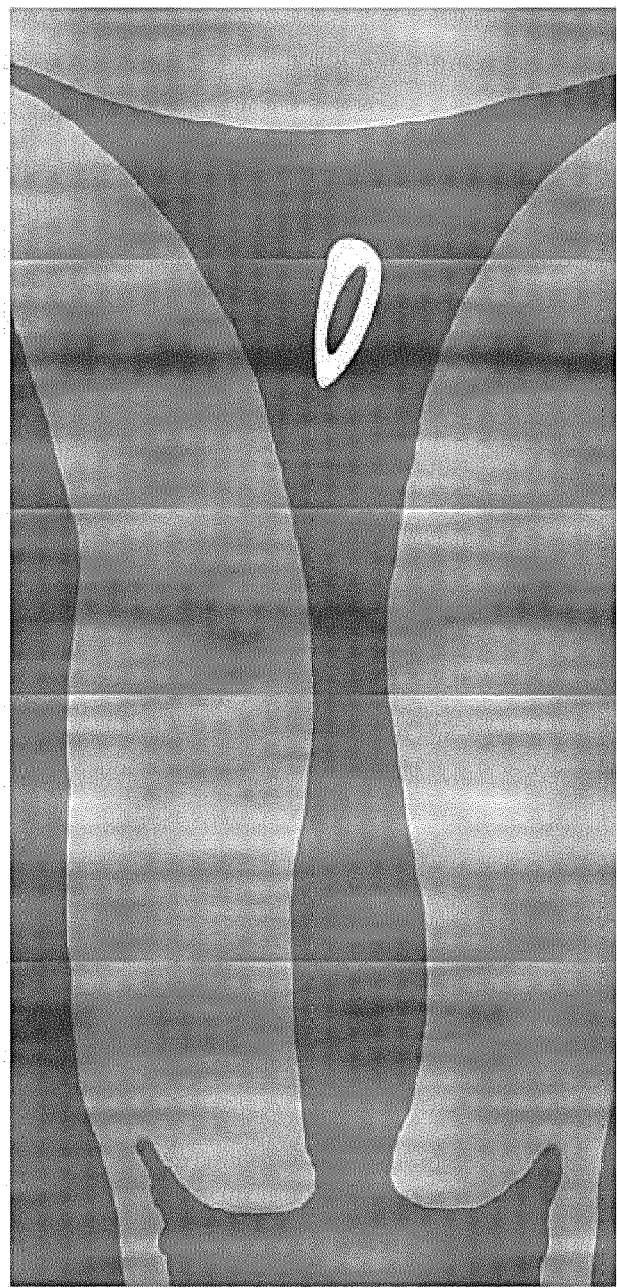
Figure 28:
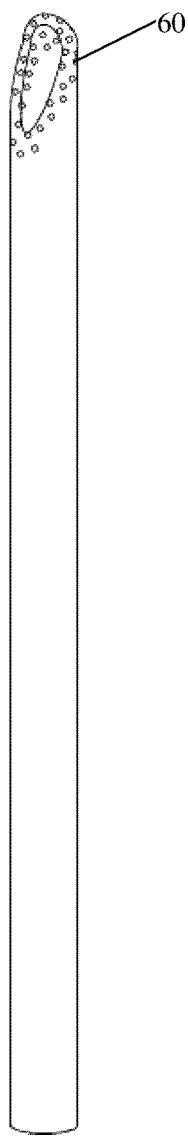
Figure 29:
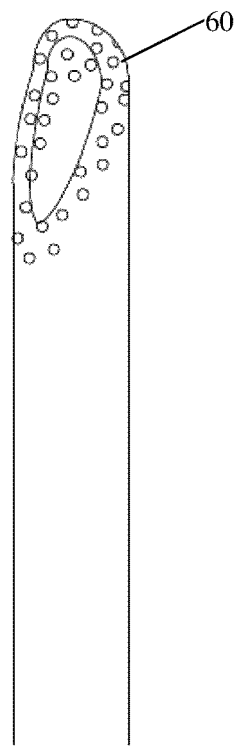
Figure 30:
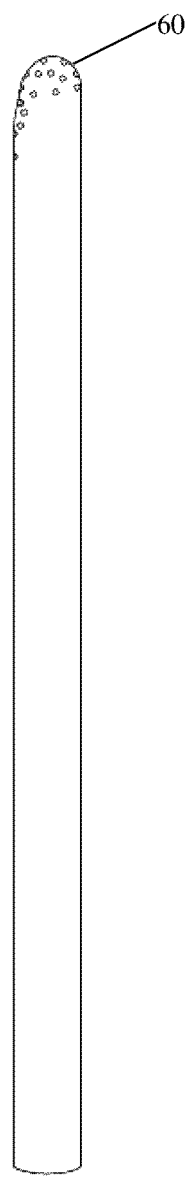
Figure 31:
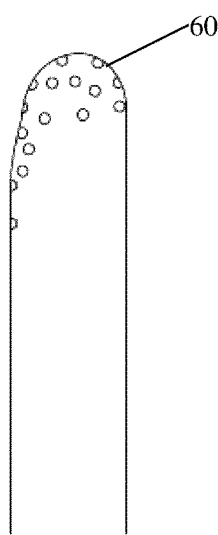
Figure 32:
Figure 33:
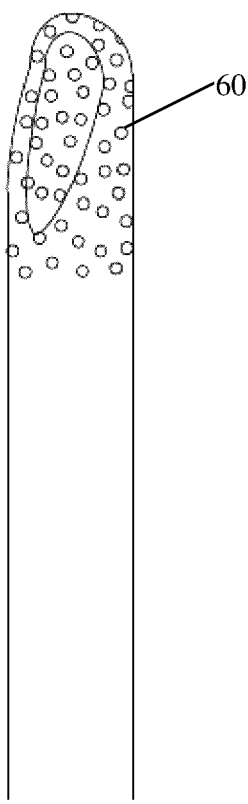
Figure 34:
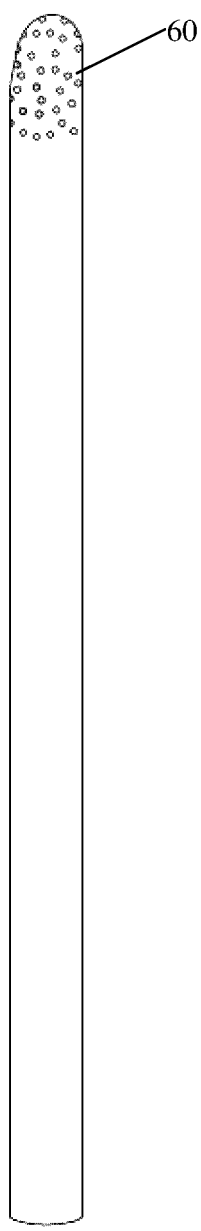
Figure 35:
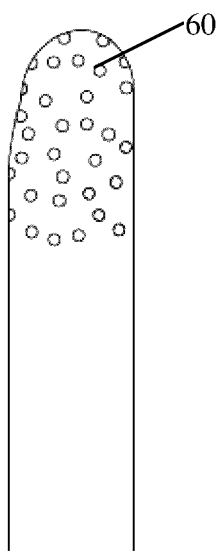
Figures 36, 37, 38, 39:
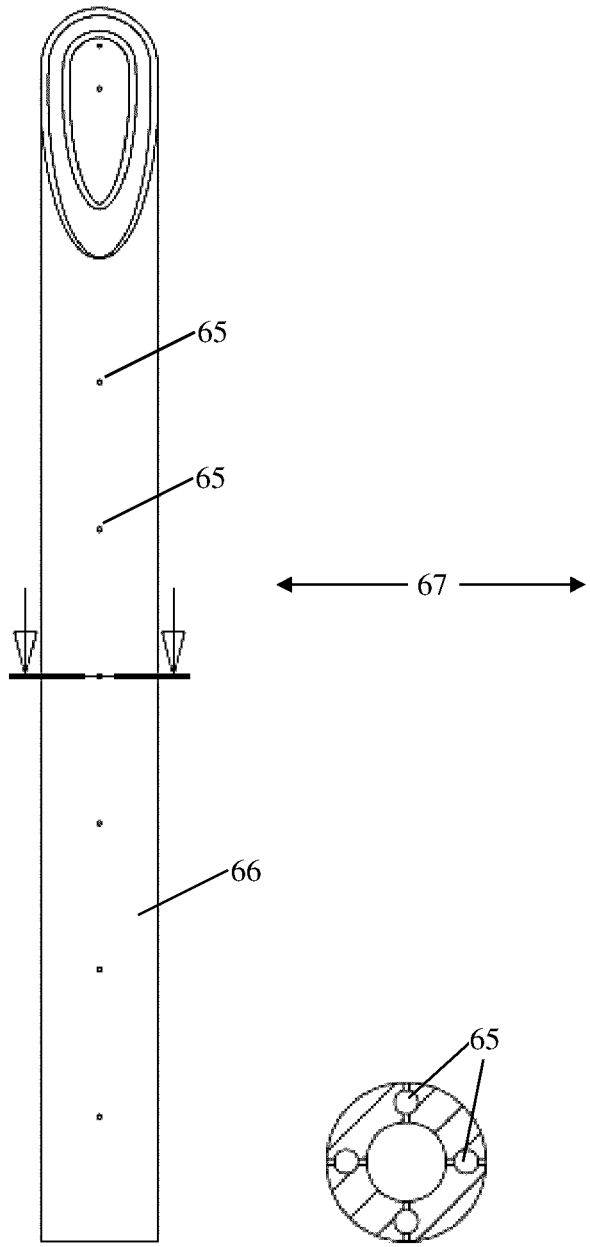
FIGS. 36 to 39 are images of another curette with echogenic features in the form of voids.

FIGS. 21 to 23 illustrate another curette 40 which, in this case, comprises a distal opening 41 with a lip 42 which is rendered echogenic by selecting a suitable material and/or finish.

FIGS. 24 to 27 illustrate a further curette 50 which has a lip filled with material such as polystyrene balls 51 or the like which has a different echogenic property to that of the main body of the shaft 52. The tip may be overmoulded with a suitable shaft material such as polycarbonate. A similar effect may be achieved using a tip of a closed cell material and/or by providing voids in the main body of the curette shaft.

FIGS. 28 to 31 and 32 to 35 illustrate other echogenic curette tips 60.

FIGS. 28 to 31 illustrate a curette which is moulded with bubbles focused around the opening of the curette. Alternatively, a separate element with bubbles may be attached/welded/glued/overmoulded onto a main shaft.

FIGS. 32 to 35 illustrate a curette which is moulded with a greater concentration of bubbles focused around the head of the curette. Alternatively, a separate element with bubbles may be attached/welded/glued/overmoulded onto a main shaft.

Figure 40:
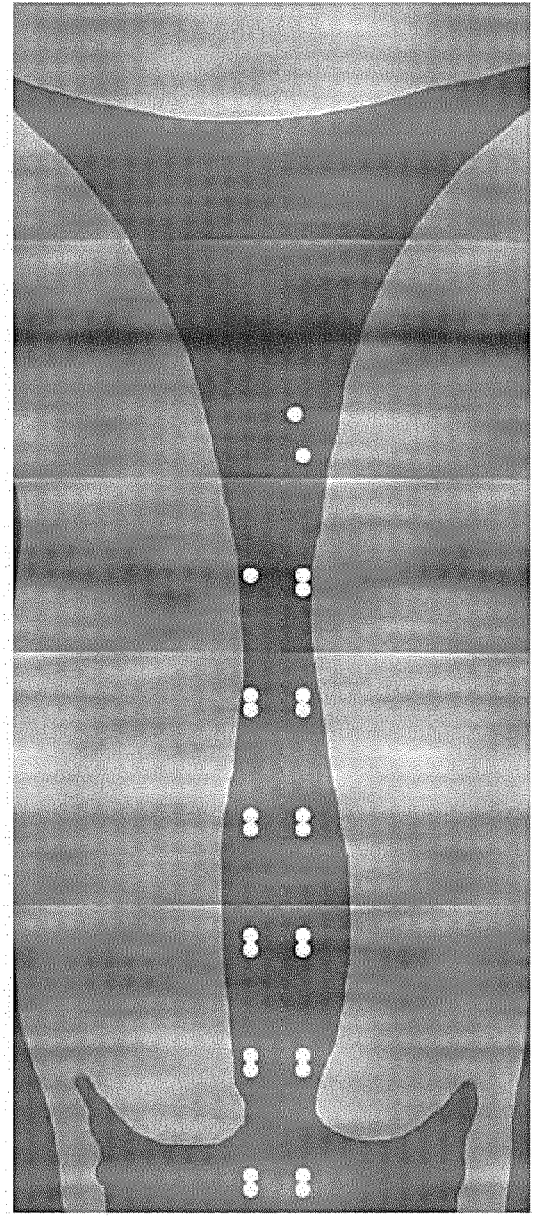
FIGS. 40 and 41 are ultrasound images of a curette of FIGS. 36 to 39 in use with empty voids (FIG. 40) or voids filled with fluid (FIG. 41)
Figure 41:
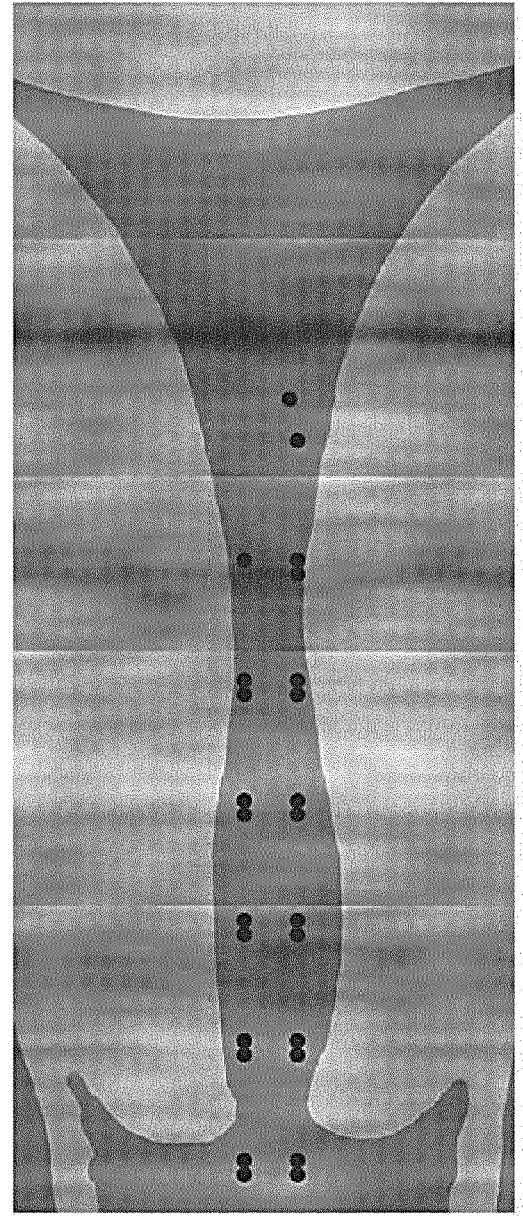

Referring to FIGS. 36 to 39, in this case voids such as empty spheres 65 may be moulded into the shaft 66 of a curette 67 to enhance echogenicity. Alternatively, at least some of the voids may be filled with a fluid. FIGS. 40 and 41 illustrate a curette in use with empty voids (FIG. 40) and filled voids (FIG. 41) in the shaft under ultrasound.

Figures 42, 43, 44, 45, 46:
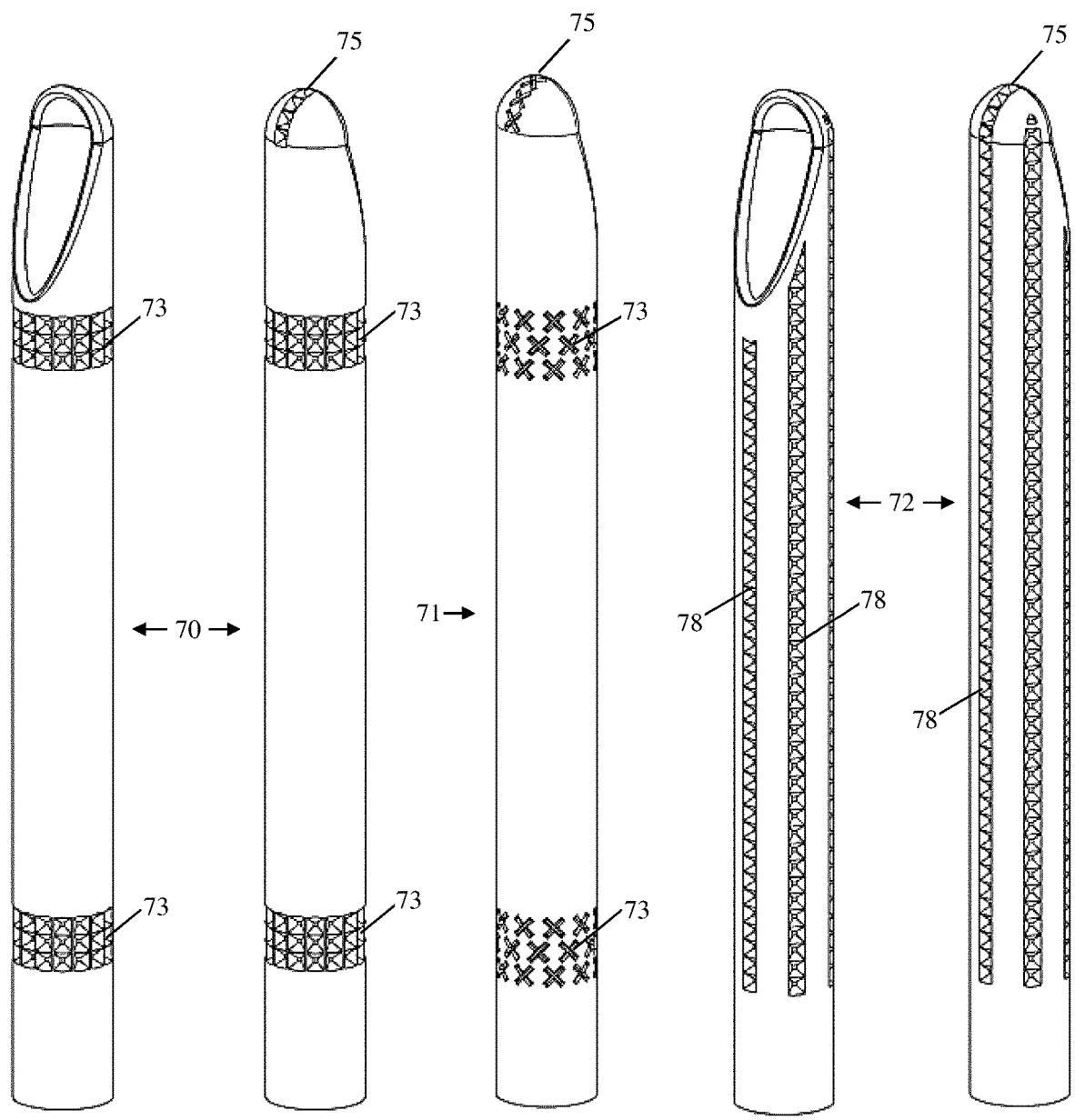
FIGS. 42 to 44 are images of a curette with echogenic features etched or moulded therein or thereon.
FIGS. 45 and 46 illustrate another curette with echogenic features extending along the shaft.

FIGS. 42 to 44 illustrate curettes 70, 71 with various patterns 73 provided in or on the curette. The patterns 73 may be moulded into the curette or may be formed by cutting, such as by etching. The pattern may be of any shape such as those with sharp edges, for example, inverted pyramids or X shapes. In some cases, an echogenic pattern extends over the distal tip of the curette, somewhat like a stripe or a mohawk 75.

Another echogenic pattern 78 in a curette 72 is illustrated in FIGS. 45 and 46. The linear shapes extending longitudinally along the shaft of the curette 72 assist in conveying rotation under ultrasound thereby assisting in showing the orientation of the distal opening.

Figure 47:
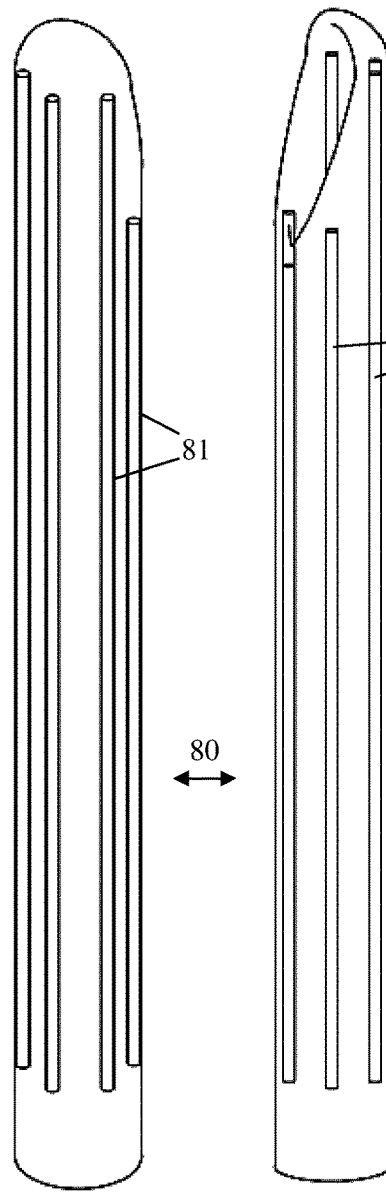
FIGS. 47 to 50 are images of a curette with elongate voids in the form of ribs or rods extending along the shaft.
Figure 48:
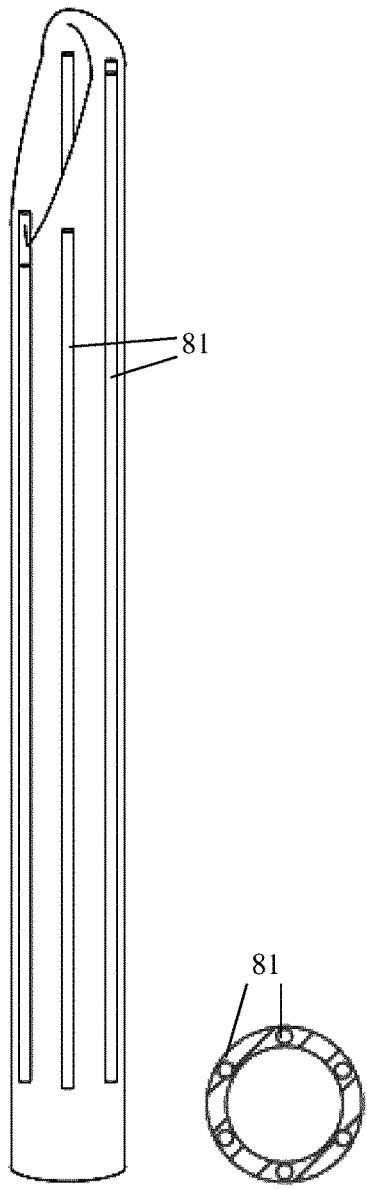
Figure 49:
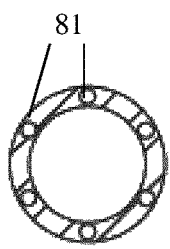
Figure 50:
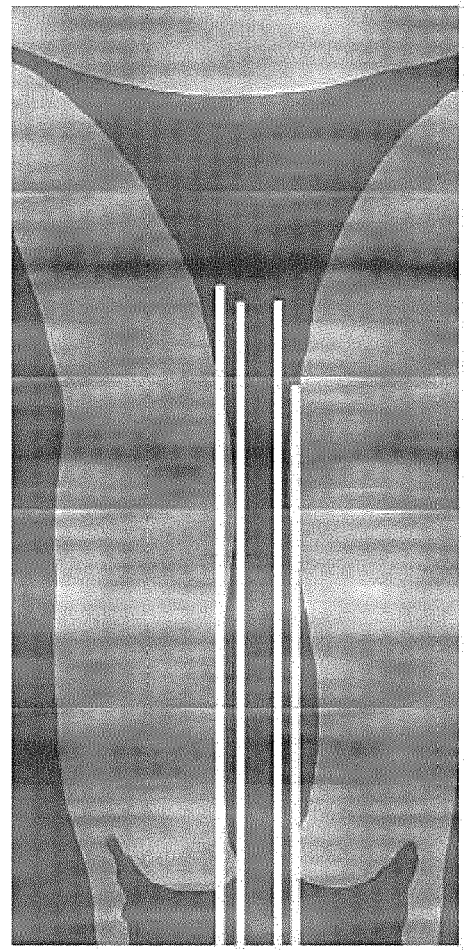

Referring to FIGS. 47 and 48, there is illustrated a curette 80 with either moulded empty cavities in the shaft, overmoulded echogenic ribs or rods, and/or fluid filled linear cavities 81. FIG. 50 illustrates the appearance of the ribs 81 under ultrasound.

Figure 51:
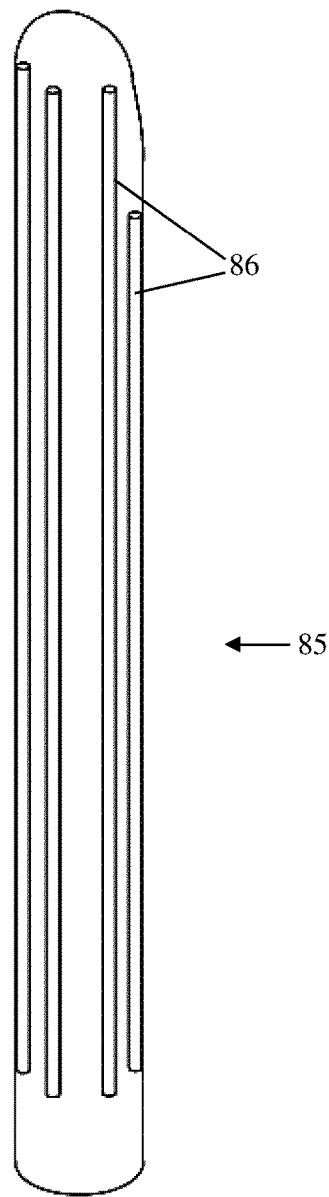
FIGS. 51 and 52 are views similar to FIGS. 47 to 50 with the elongate ribs or rods filled with a fluid.
Figure 52:
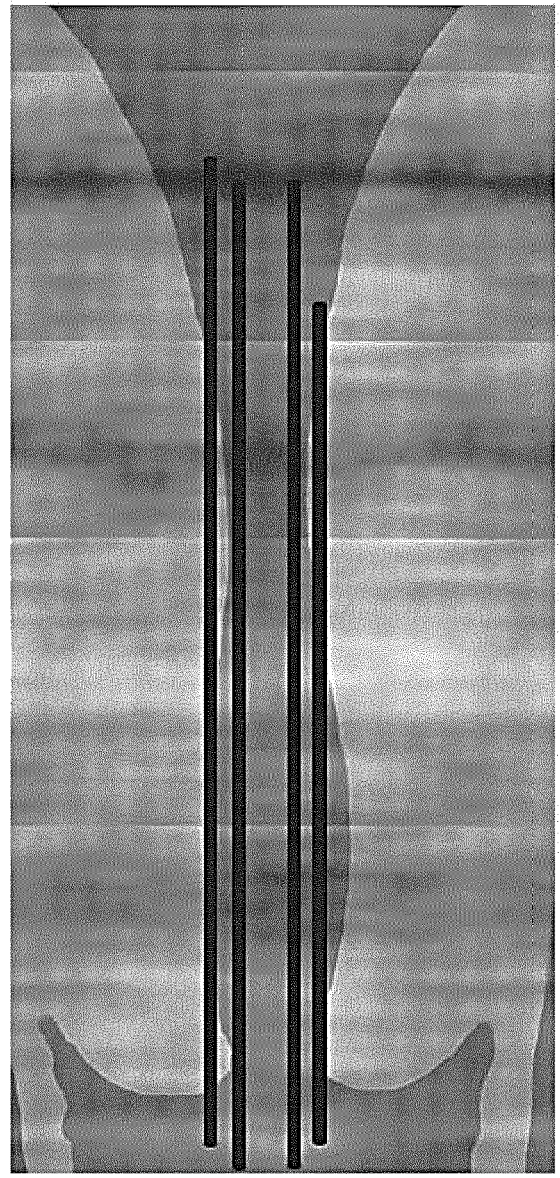

FIG. 51 illustrates a curette 85 with linear cavities 86 which may be filled with fluid. FIG. 52 illustrates the appearance of the fluid filled cavities 86 under ultrasound.

Figure 53:
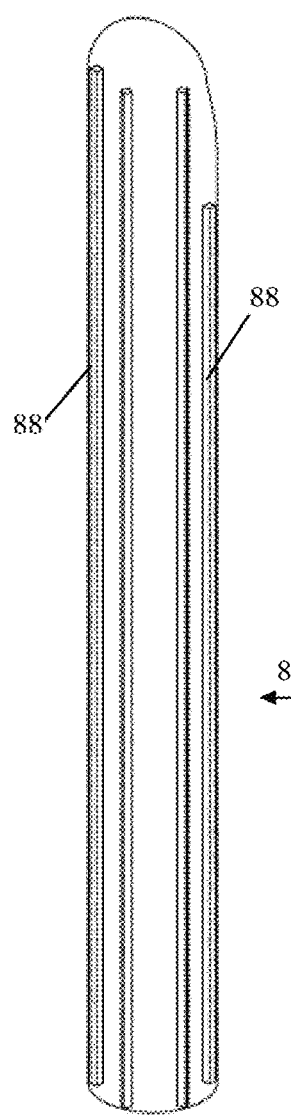
FIGS. 53 to 56 are views of an echogenic curette similar to FIGS. 47 to 52 with ribs or rods having sharp corners.
Figure 54:
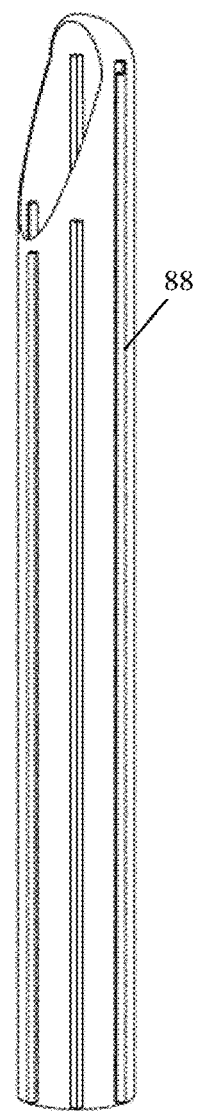
Figure 55:
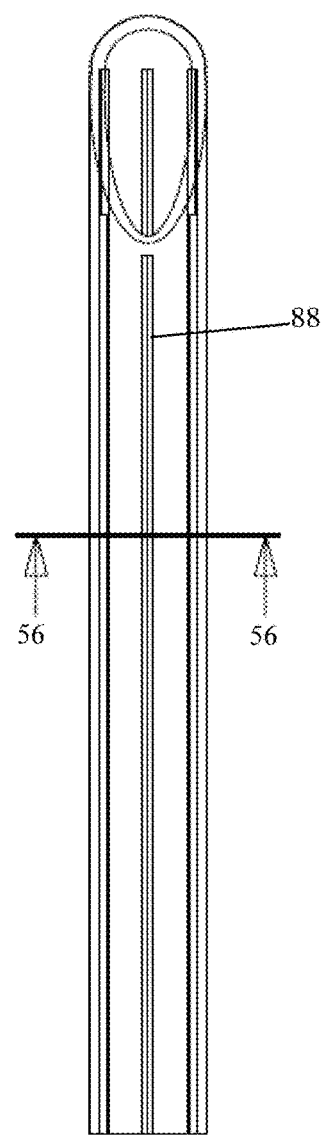
Figure 56:
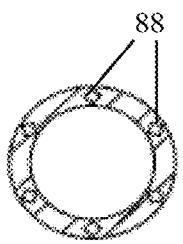
Figure 57:
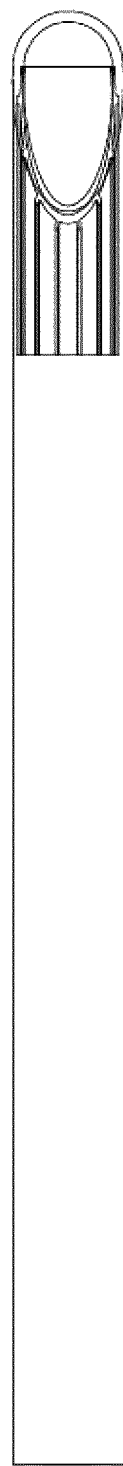
FIGS. 57 to 60 are images of a further curette with an overmoulded distal tip of an echogenic material such as polystyrene.
Figure 58:
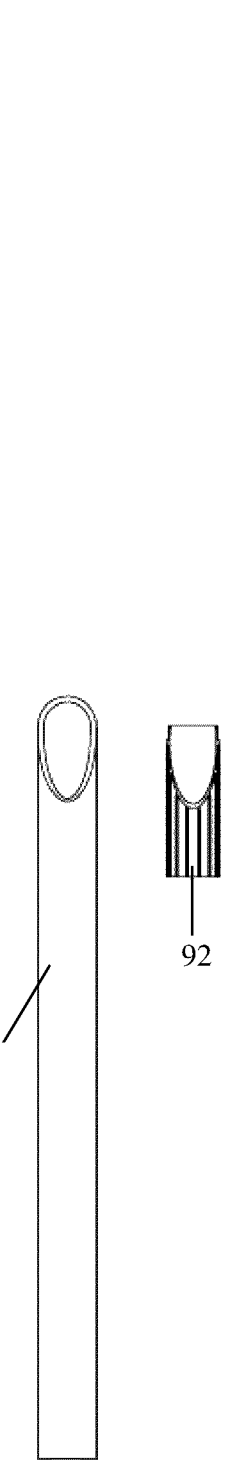
Figure 59:
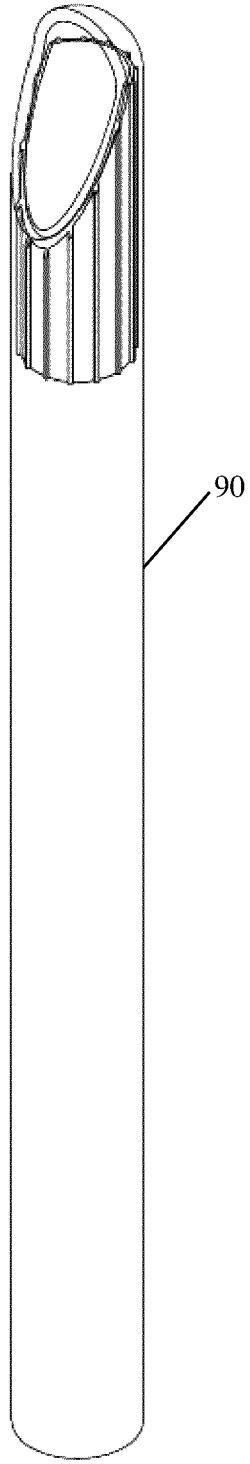
Figure 60:
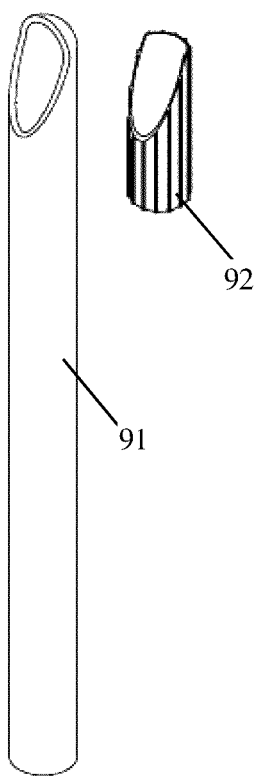

FIGS. 53 to 55 illustrate curettes 87 similar to those illustrated in FIG. 47, FIG. 48 and FIG. 51. In this case, cavities or ribs 88 have a cross section with sharp corners. The sharp corners may enhance visibility under ultrasound.

FIGS. 57 to 60 illustrate further curettes 90 of over-moulded construction comprising a shaft 91 and a distal component 92 of a suitable echogenic material such as polystyrene.

We have found that a curette 95 including a rigid foam distal component 96 has excellent echogenic properties. One such curette 95 is illustrated in FIGS. 61 to 63.

Figure 64:
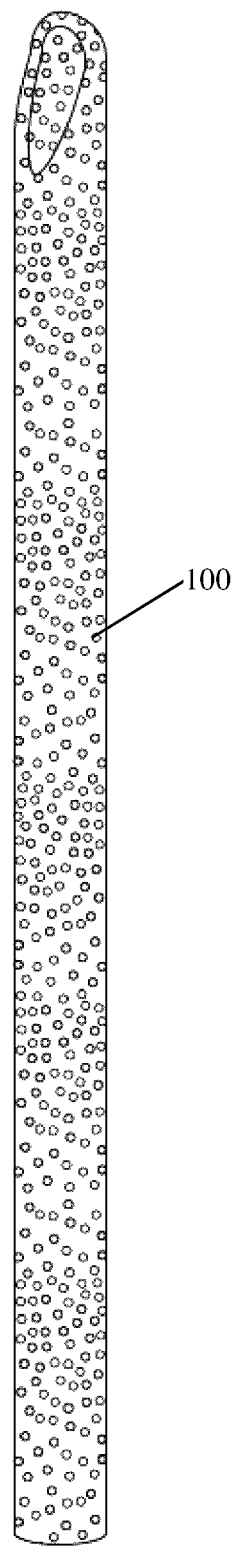
FIGS. 64 and 65 are views of a curette with bubbles extending through the length of the curette.
Figure 65:
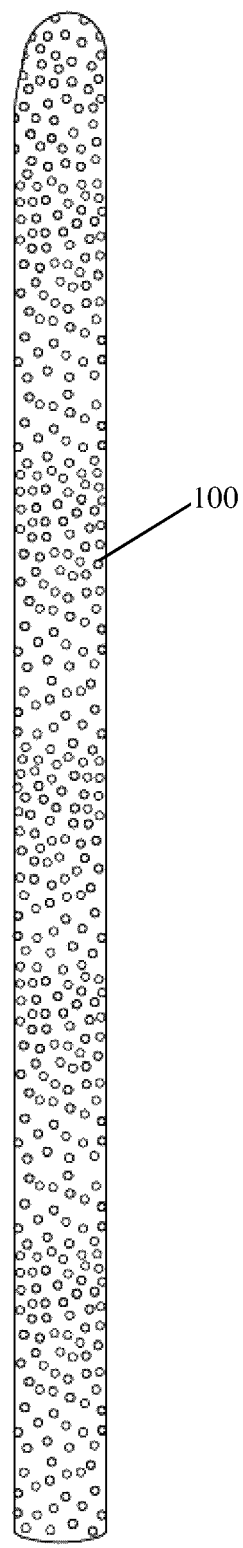
Figure 66:
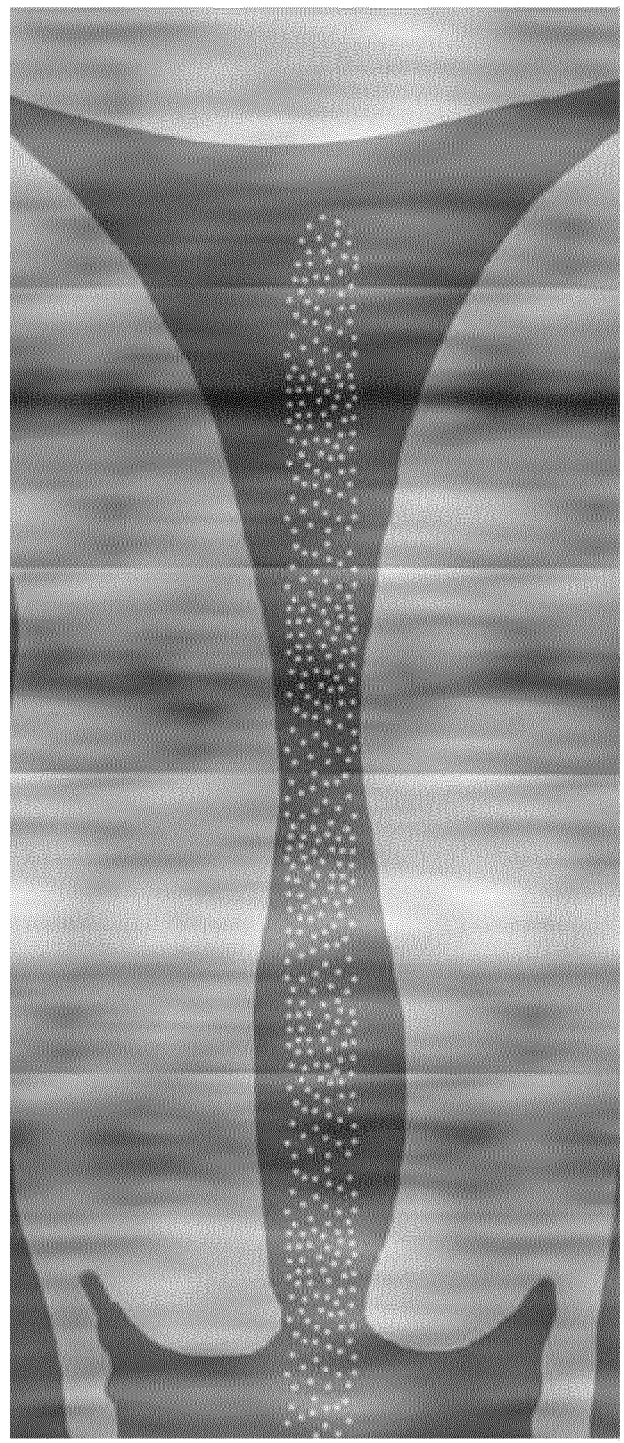
FIG. 66 is a view of the curette of FIGS. 64 and 65, in use.

FIGS. 64 and 65 illustrate a curette 100 in which the entire component has bubbles along the length thereof. FIG. 66 illustrates the curette 100 of FIGS. 64 and 65, in use.

FIGS. 67 and 68 illustrate a curette 105 with a spark pattern along the length of the curette. Any suitable spark pattern may be used.

Figure 69:
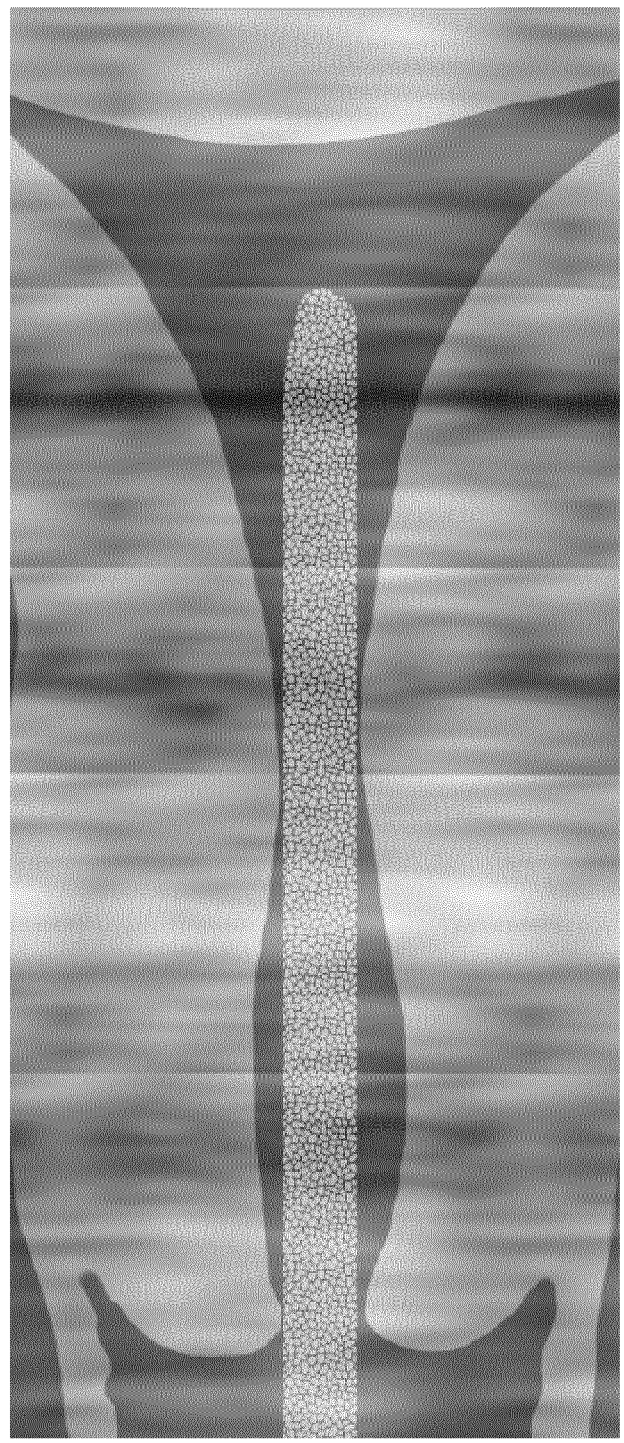
FIG. 69 is an X-ray of the curette of FIG. 68, in use.
Figures 70, 71, 72, 73, 74, 75, 76, 77:
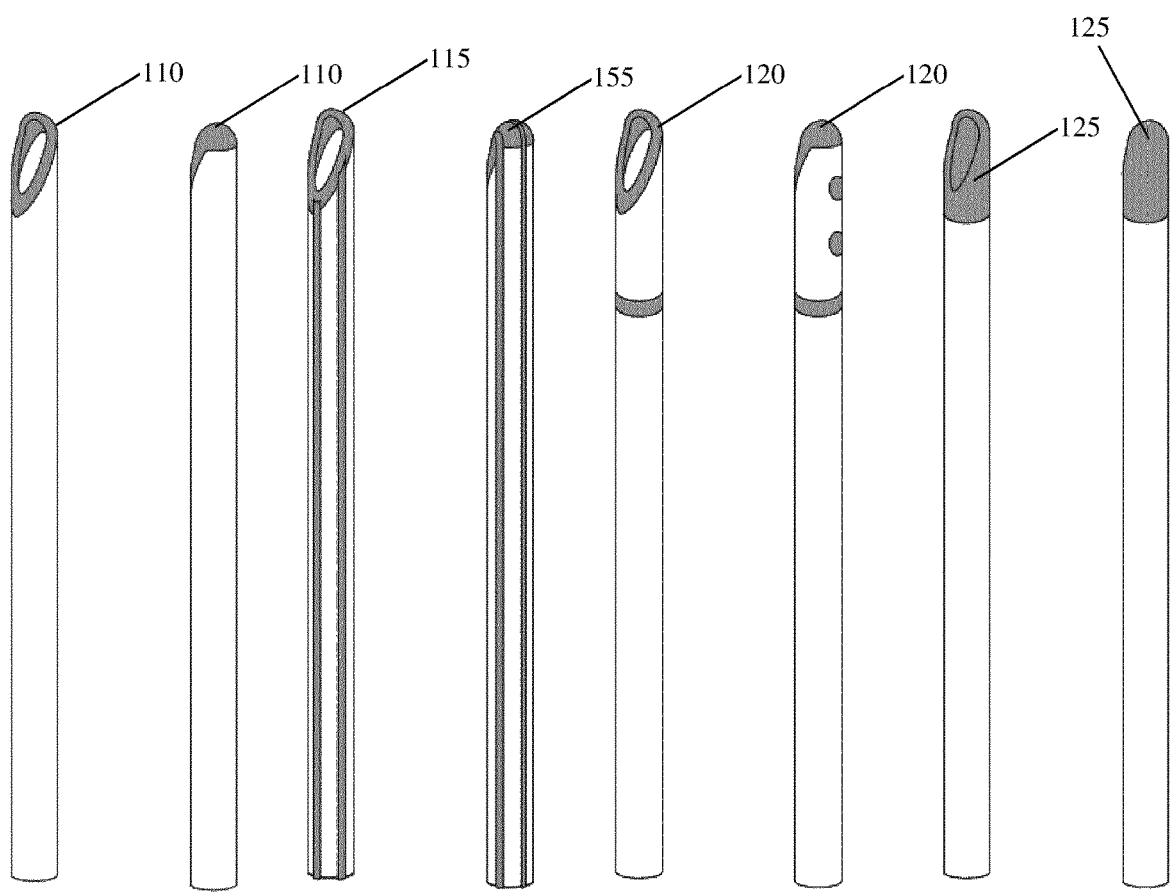
FIGS. 70 to 77 are views of curettes with various spark patterns.
Figure 83:
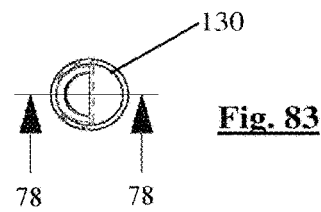
FIGS. 78 to 84 are views of a curette with a spiral rib.
Figure 78:
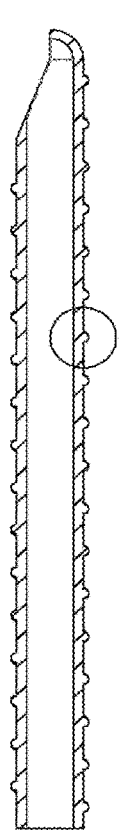
Figure 79:
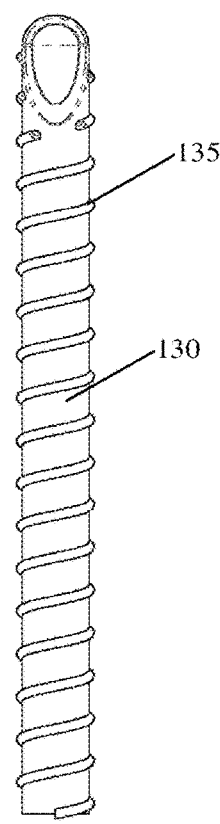
Figure 80:
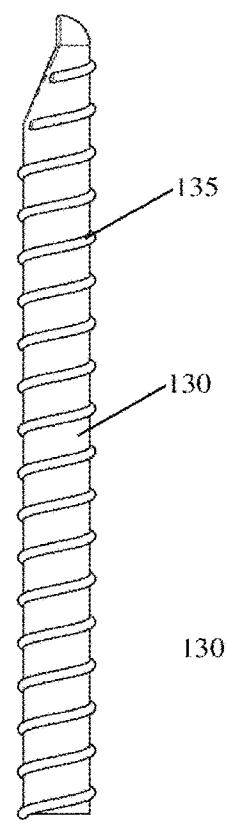
Figures 81, 82:
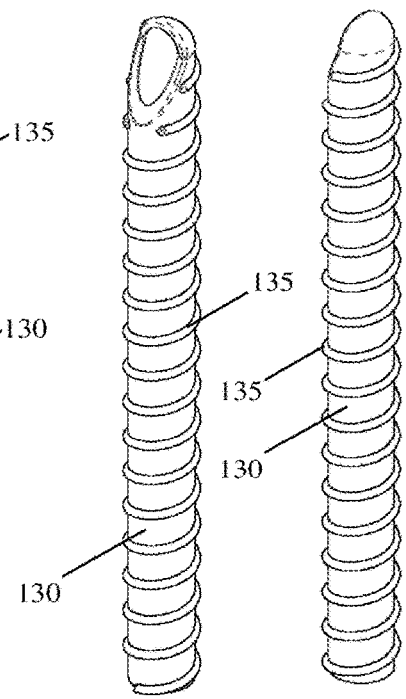
Figure 84:
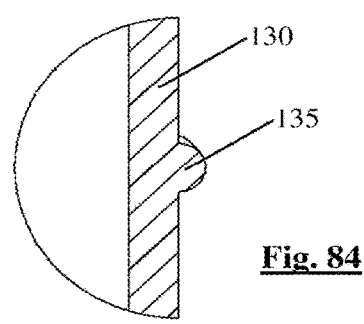
Figure 97:
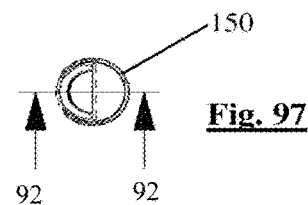
FIGS. 92 to 98 are views of a curette with a higher frequency of ribs.
Figure 92:
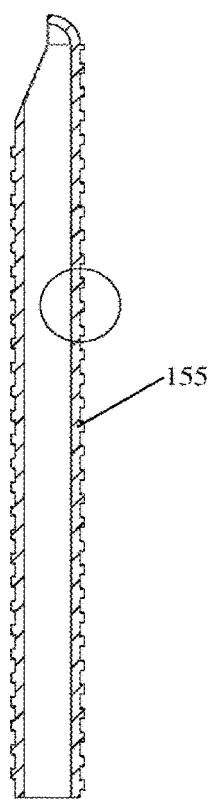
Figure 93:
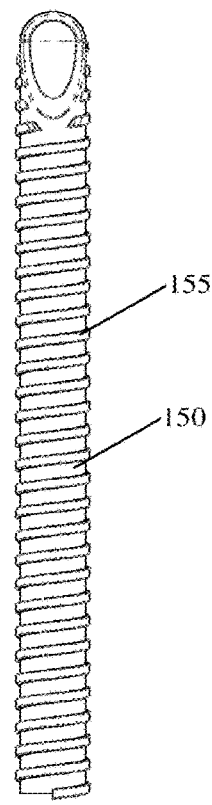
Figure 94:
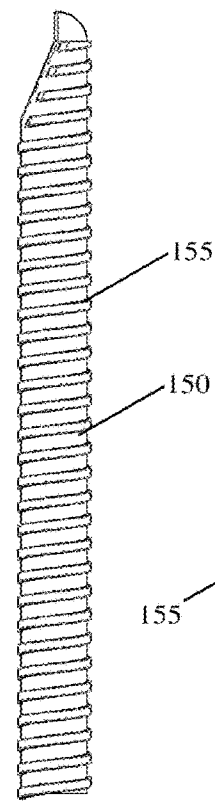
Figures 95, 96:
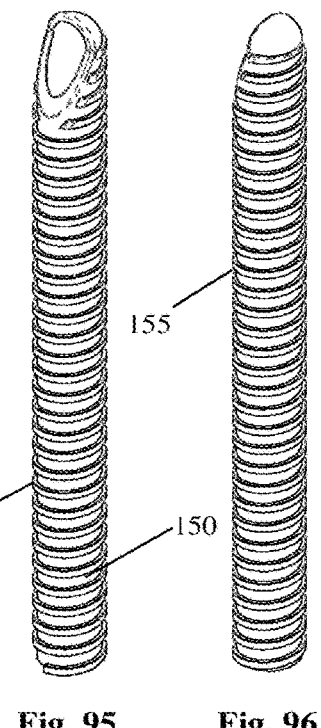
Figure 98:
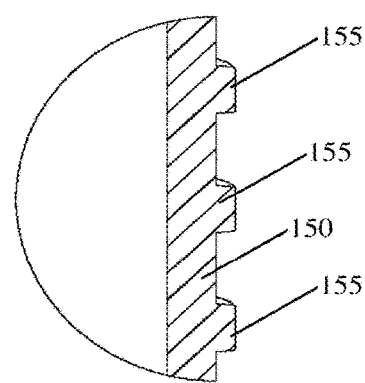
Figure 118:
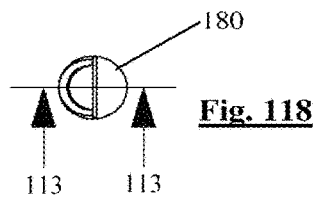
FIGS. 113 to 119 are views of a curette with a V-shaped spiral groove.
Figure 113:
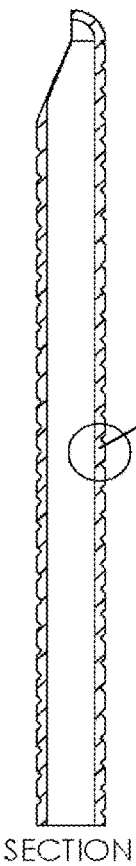
Figure 114:
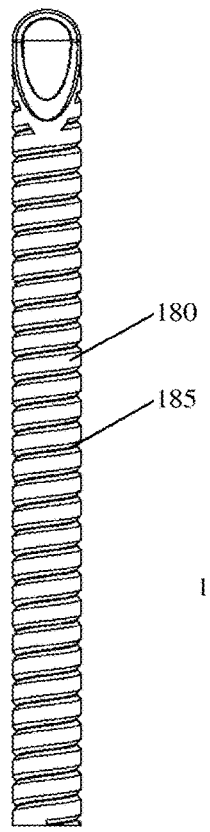
Figure 115:
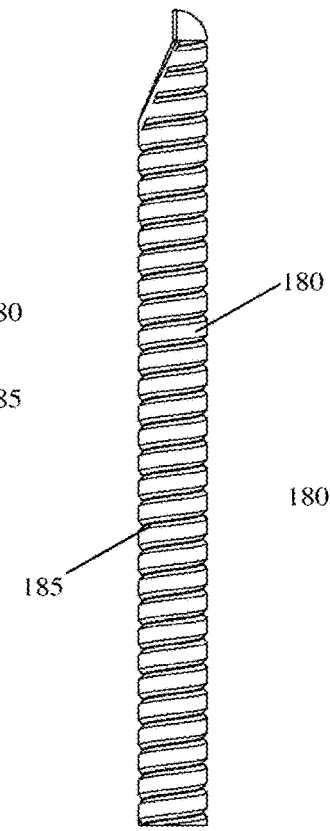
Figure 116:
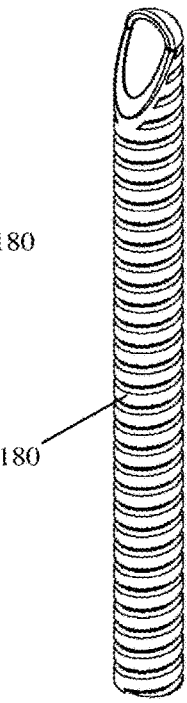
Figure 117:
Figure 119:
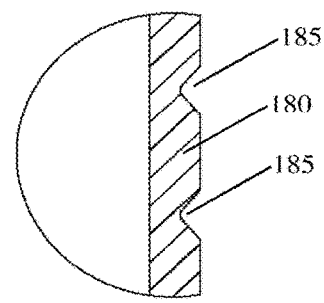
Figure 125:
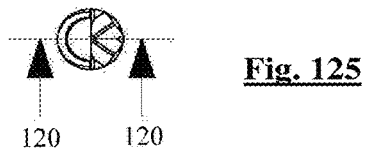
FIGS. 120 to 127 are views of a curette with spiral V-shaped grooves turning in opposite directions.
Figure 120:
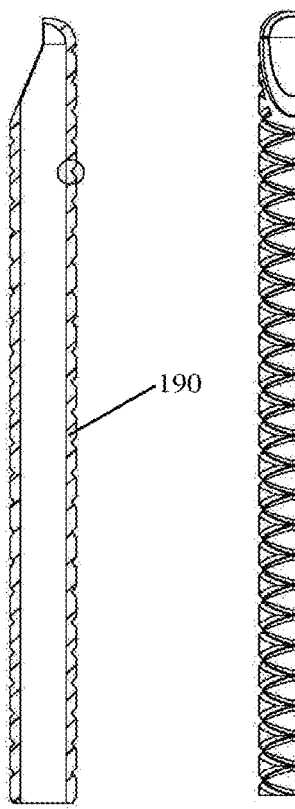
Figures 121, 122:
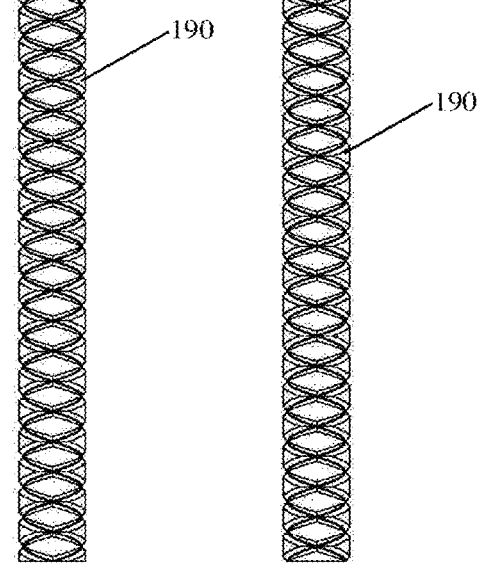
Figures 123, 124:
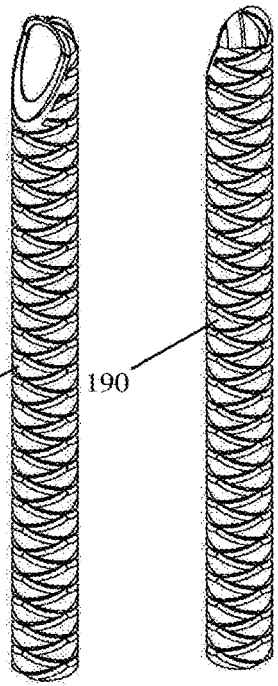
Figure 127:
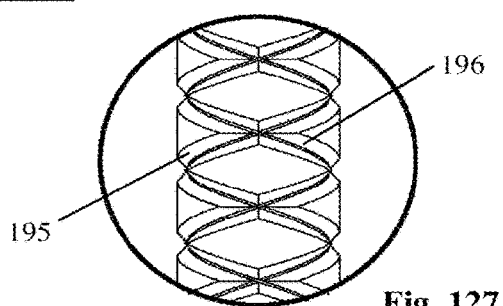
Figure 126:
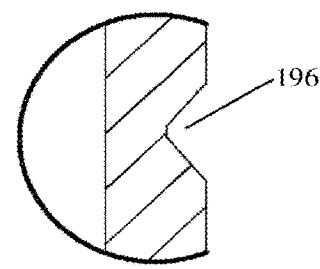
Figures 135, 136, 137, 138, 139, 140:
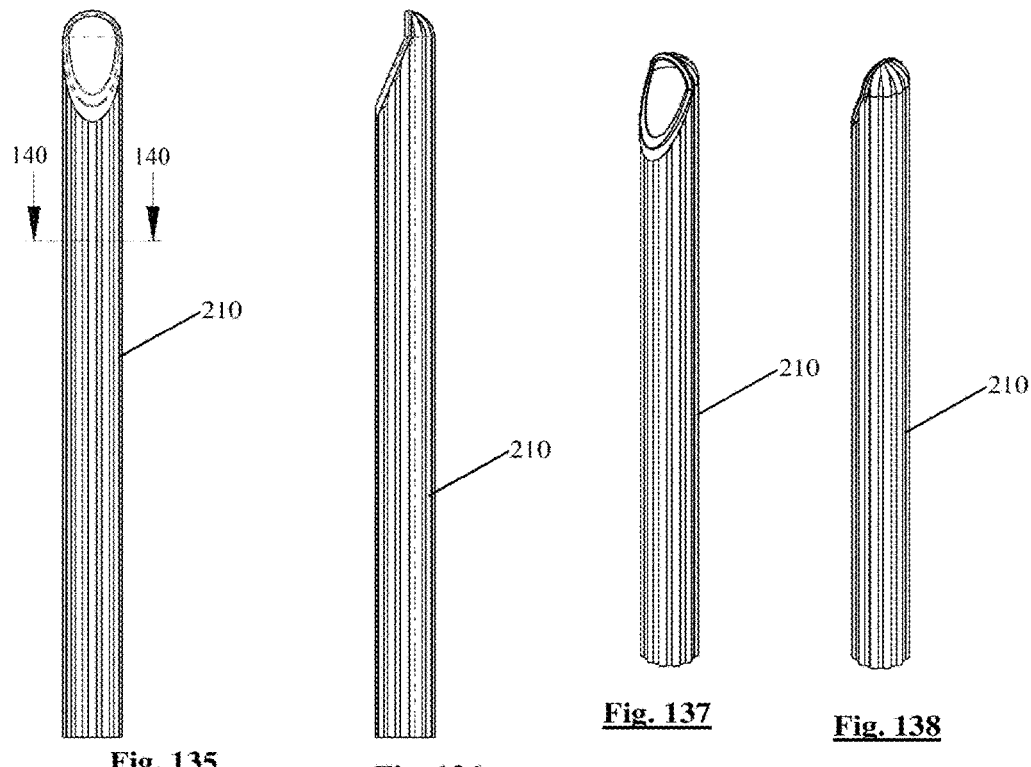
FIGS. 135 to 140 are views of a curette with a greater number of rounded ribs.

FIG. 69 illustrates the curette 105 of FIGS. 67 and 68 in use. The spark finish provides a full visible image of the curette.

As illustrated in FIGS. 70 to 77, a spark finish may be applied in a number of different patterns 110, 115, 120, 125 at the distal end and/or along at least portion of the length of the curette.

Referring to FIGS. 78 to 84, there is illustrated a curette 130 with a rib 135, in this case in a spiral along at least portion of the length of the curette. In one case the rib 135 is of hemispherical shape and may have a diameter of about 1.6 mm. There may be a high or low frequency of revolutions.

Referring to FIGS. 85 to 91 in an alternative a curette 140 has a rib 145 which in this case is rectilinear such as square shaped. Sharp edges aid echogenicity. There may be a high or low frequency of revolutions.

Referring to FIGS. 92 to 98 illustrate a curette 150 with ribs 155 having sharp edges to aid echogenicity. The ribs 155 in this case are in a spiral pattern with a higher frequency than in the curette of FIGS. 85 to 91.

Referring to FIGS. 99 to 105, in this case a curette 160 has cut-in lines or grooves 165. Again the sharp edges of the long ribs greatly increase the visibility of the device especially as it is being rotated, in use.

Referring to FIGS. 106 to 112, in this case a curette 170 has a flat rectilinear spiral groove 175 to create sharp edges for enhanced echogenicity.

Alternatively, as illustrated in FIGS. 113 to 119 a curette 180 may have a V shaped spiral groove 185 to create sharp edges for enhanced echogenicity.

There may be several grooves and/or ribs along at least portion of the curette. For example, and referring to FIGS. 120 to 127, there may be two spiral V grooves 195, 196 turning in opposite directions to give a hatched effect for increased visibility of a curette 190.

Referring to FIGS. 128 to 134, a curette 200 may have one or more ribs or grooves 205 which extend circumferentially around the curette 200, for example near the distal end of the curette 200. These features provide resistance as the curette 200 is being inserted into the cervix. The surgeon feels the resistance reducing as the rings 205 clear the cervix channel. The ribs/grooves 205 also enhance visibility of the curette 200 as it is advanced into the uterus.

FIGS. 135 to 140 illustrate a curette 210 with rounded ribs 215 extending along a length of the curette 210. A higher frequency of ribs enhances visibility. The curette may have a relatively thin wall section with the ribs increasing the outer diameter. This curette may also include bubbles which may be formed as the curette is being formed from a plastics material. The ribs greatly enhance visibility when the curette is rotated.

The invention is not limited to the embodiments hereinbefore described which may be varied in detail.

The invention claimed is:

1. A method of using a curette when performing a suction dilation and curettage on a patient, the curette including a shaft having a distal end with a distal opening, a proximal end with a proximal opening, and a lumen extending between the proximal opening and the distal opening; and the distal end including a rounded tip and at least a portion of an outer surface of the distal end has echogenic features, the method comprising:
   deploying the curette into a vagina of the patient;
   inserting the curette into a cervix and a uterus of the patient under ultrasound guidance, the ultrasound guidance being based on the echogenic features of the distal end of the shaft;
   rotating the curette;
   displaying a rotational orientation of the distal opening of the shaft based on ultrasound and the echogenic features during the rotating of the curette;
   performing uterine evacuation under ultrasound guidance; and
   withdrawing the curette from the cervix and vagina.

2. The method of claim 1, further including dilating a cervix to a desired diameter prior to deploying the curette.

3. The method of claim 1, further including deploying the ultrasound abdominally.

4. The method of claim 1, further including deploying the ultrasound vaginally.

5. The method of claim 1, further including confirming, using the ultrasound, that a uterus of the patient is emptied.

6. The method of claim 5, further including inserting a retractor into the vagina and retracting the vagina.

7. The method of claim 6, further including removing the retractor from the vagina after withdrawing the curette from the cervix.

8. A method of using a curette when performing a suction dilation and curettage on a patient, the curette including a shaft having a distal end with a rounded tip and distal opening, a proximal end with a proximal opening, and a lumen extending between the proximal opening and the distal opening; and the distal end including a rounded tip and at least a portion of an outer surface of the distal end has echogenic features, the method comprising:
   inserting a retractor into a vagina of the patient;
   deploying the curette into the vagina;
   inserting the curette into a cervix and a uterus of the patient under ultrasound guidance with the echogenic features;
   rotating the curette;
   displaying a rotational orientation of the distal opening of the shaft based on ultrasound and the echogenic features during the rotating of the curette
   performing a suction dilation and curettage with the curette under ultrasound guidance;
   withdrawing the curette from the cervix and vagina; and
   withdrawing the retractor from the vagina.

9. The method of claim 8, further including deploying the ultrasound abdominally.

10. The method of claim 8, further including deploying the ultrasound vaginally.

11. The method of claim 8, further including confirming, using the ultrasound, that a uterus of the patient is emptied.

12. The method of claim 8, further including dilating a cervix to a desired diameter prior to deploying the curette.

13. A method of using a curette when performing a suction dilation and curettage on a patient, the curette including a shaft having a distal end with a distal opening, a proximal end with a proximal opening, and a lumen extending between the proximal opening and the distal opening; and the distal end including a rounded tip and at least a portion of an outer surface of the distal end has echogenic features, the echogenic features being cavities and/or bubbles, wherein the only portion of the shaft with echogenic features is the distal end, the method comprising:

inserting a retractor into a vagina of the patient;

stabilizing a cervix of the patient using a cervical stabilizer;

inserting the curette into the cervix and a uterus under ultrasound guidance with the echogenic features:

rotating the curette;

displaying a rotational orientation of the distal opening of the shaft based on ultrasound and the echogenic features during the rotating of the curette;

performing uterine evacuation under ultrasound guidance;

withdrawing the curette from the vagina;

withdrawing the cervical stabilizer from the cervix; and withdrawing the retractor from the vagina.

14. The method of claim 13, further including dilating a cervix to a desired diameter prior to deploying the curette.

15. The method of claim 13, further including confirming, using the ultrasound, that a uterus of the patient is emptied.

16. The method of claim 13, further including deploying the ultrasound abdominally.

17. The method of claim 13, further including deploying the ultrasound vaginally.

\* \* \* \* \*